US008657793B2

(12) United States Patent
Pellegrini et al.

(10) Patent No.: US 8,657,793 B2
(45) Date of Patent: Feb. 25, 2014

(54) SPACE SAVING PLUNGER CAP AND ROD ASSEMBLY

(71) Applicant: Becton Dickinson France, S.A.S., Le Pont-de-Claix (FR)

(72) Inventors: James Pellegrini, Cary, NC (US); Darrin Scott Manke, North Andover, MA (US); Christopher Labak, Brookline, NH (US); Joseph Omer St. Cyr, Salem, NH (US)

(73) Assignee: Becton Dickinson France, S.A.S, Le Pont-de-Claix (FR)

( * ) Notice: Subject to any disclaimer, the term of this patent is extended or adjusted under 35 U.S.C. 154(b) by 0 days.

(21) Appl. No.: 13/622,376

(22) Filed: Sep. 19, 2012

(65) Prior Publication Data

US 2013/0085446 A1 Apr. 4, 2013

Related U.S. Application Data

(60) Provisional application No. 61/541,633, filed on Sep. 30, 2011.

(51) Int. Cl.
*A61M 5/00* (2006.01)

(52) U.S. Cl.
USPC .......................................................... 604/187

(58) Field of Classification Search
USPC ......................................... 604/187, 110–111
See application file for complete search history.

(56) References Cited

U.S. PATENT DOCUMENTS

| 1,512,294 A | 10/1924 | Marcy |
| 1,971,687 A | 8/1934 | Kratz |
| 2,672,142 A | 3/1954 | Melton |
| 2,672,868 A | 3/1954 | Hickey |
| 2,871,858 A | 2/1959 | Dann et al. |
| 3,342,319 A | 9/1967 | Faulseit |
| 3,353,664 A | 11/1967 | Armentrout et al. |
| 3,473,646 A | 10/1969 | Burke |
| 4,011,868 A | 3/1977 | Friend |
| 4,184,593 A | 1/1980 | Dorr |
| 4,636,202 A | 1/1987 | Lowin et al. |
| 4,743,234 A | 5/1988 | Leopoldi et al. |

(Continued)

FOREIGN PATENT DOCUMENTS

| EP | 0568207 A1 | 11/1993 |
| EP | 0605422 A1 | 7/1994 |

(Continued)

*Primary Examiner* — Nicholas Lucchesi
*Assistant Examiner* — Melissa A Snyder
(74) *Attorney, Agent, or Firm* — The Webb Law Firm

(57) ABSTRACT

A syringe assembly includes a syringe barrel defining a chamber and having a stopper disposed within the chamber, a sleeve having a first end and a second end and extending at least partially about the syringe barrel, and a cap associated with a second end of the sleeve. The syringe assembly also includes a plunger rod having a first end associated with the cap and a second end, wherein the plunger rod is transitionable from a pre-use position, in which at least a portion of the second end of the plunger rod extends along a portion of a barrel sidewall, to a ready-to-use position in which the plunger rod is aligned with the stopper. Upon proximal movement of the sleeve in a direction away from a first end of the barrel, the plunger rod is configured for lateral movement with respect to the cap into the ready-to-use position.

28 Claims, 24 Drawing Sheets

(56) References Cited

U.S. PATENT DOCUMENTS

| | | | |
|---|---|---|---|
| 5,000,744 A | 3/1991 | Hoffman et al. | |
| 5,176,657 A | 1/1993 | Shields | |
| 5,226,884 A | 7/1993 | Murphy | |
| 5,308,330 A | 5/1994 | Grimard | |
| 5,344,405 A | 9/1994 | Richards | |
| 5,354,285 A | 10/1994 | Mazurik et al. | |
| 5,407,070 A | 4/1995 | Bascos et al. | |
| 5,411,489 A | 5/1995 | Pagay et al. | |
| 5,413,563 A | 5/1995 | Basile et al. | |
| 5,423,757 A | 6/1995 | Olovson et al. | |
| 5,453,093 A | 9/1995 | Haining | |
| 5,478,324 A | 12/1995 | Meyer | |
| 5,558,650 A | 9/1996 | McPhee | |
| 5,573,514 A | 11/1996 | Stiehl et al. | |
| 5,643,213 A | 7/1997 | McPhee | |
| 5,700,246 A | 12/1997 | Stiehl et al. | |
| 5,700,247 A | 12/1997 | Grimard et al. | |
| 5,722,951 A | 3/1998 | Marano | |
| 5,807,323 A | 9/1998 | Kriesel et al. | |
| 5,897,532 A | 4/1999 | Spallek et al. | |
| 5,938,642 A | 8/1999 | Burroughs et al. | |
| 6,001,089 A | 12/1999 | Burroughs et al. | |
| 6,059,756 A | 5/2000 | Yeh | |
| 6,086,568 A | 7/2000 | Caizza | |
| 6,171,286 B1 | 1/2001 | Gross | |
| 6,228,324 B1 | 5/2001 | Hasegawa et al. | |
| 6,231,550 B1 * | 5/2001 | Laughlin | 604/187 |
| 6,338,200 B1 | 1/2002 | Baxa et al. | |
| 6,344,031 B1 | 2/2002 | Novacek et al. | |
| 6,368,303 B1 | 4/2002 | Caizza | |
| 6,485,460 B2 | 11/2002 | Eakins et al. | |
| 6,527,751 B2 | 3/2003 | Fischer et al. | |
| 6,585,690 B1 | 7/2003 | Hoeck et al. | |
| 6,585,691 B1 | 7/2003 | Vitello | |
| 6,599,269 B1 | 7/2003 | Lewandowski et al. | |
| 6,613,024 B1 | 9/2003 | Gargione | |
| 6,622,721 B2 | 9/2003 | Vedrine et al. | |
| 6,676,641 B2 | 1/2004 | Woodard, Jr. et al. | |
| 6,733,475 B2 | 5/2004 | Huang et al. | |
| 6,866,142 B2 | 3/2005 | Lamborne et al. | |
| 6,878,131 B2 | 4/2005 | Novacek et al. | |
| 6,913,592 B2 | 7/2005 | Parsons | |
| 7,011,649 B2 | 3/2006 | De La Serna et al. | |
| 7,081,107 B2 | 7/2006 | Kito et al. | |
| 7,125,394 B2 | 10/2006 | Berman et al. | |
| 7,141,036 B2 | 11/2006 | Berman et al. | |
| 7,258,119 B2 | 8/2007 | Mazzoni | |
| 7,293,803 B2 | 11/2007 | Chu | |
| 7,361,162 B2 | 4/2008 | Koller et al. | |
| 7,569,036 B2 | 8/2009 | Domkowski et al. | |
| 7,632,244 B2 | 12/2009 | Buehler et al. | |
| 7,645,267 B2 | 1/2010 | Vetter et al. | |
| 7,699,052 B2 | 4/2010 | Schiewe et al. | |
| 7,744,580 B2 | 6/2010 | Reboul | |
| 7,762,988 B1 | 7/2010 | Vitello | |
| 7,828,772 B2 | 11/2010 | Kriesel et al. | |
| 2003/0034264 A1 | 2/2003 | Hamai et al. | |
| 2005/0154354 A1 | 7/2005 | Kawasaki et al. | |
| 2005/0192534 A1 | 9/2005 | Wolbring et al. | |
| 2006/0032768 A1 | 2/2006 | Hamai et al. | |
| 2007/0250017 A1 | 10/2007 | Carred et al. | |
| 2008/0114306 A1 | 5/2008 | Bare | |
| 2008/0202961 A1 | 8/2008 | Sharp | |
| 2009/0318880 A1 | 12/2009 | Janish | |
| 2009/0326479 A1 | 12/2009 | Janish et al. | |
| 2011/0046603 A1 | 2/2011 | Felsovalyi et al. | |
| 2011/0046604 A1 | 2/2011 | Felsovalyi et al. | |

FOREIGN PATENT DOCUMENTS

| | | |
|---|---|---|
| EP | 2085213 A1 | 8/2009 |
| JP | 852210 A | 2/1996 |
| JP | 9173451 A | 7/1997 |
| JP | 9173452 A | 7/1997 |
| JP | 10277153 A | 10/1998 |
| JP | 200014779 A | 1/2000 |
| JP | 2001104475 A | 4/2001 |
| JP | 2002172166 A | 6/2002 |
| JP | 2003260136 A | 9/2003 |
| JP | 2004329635 A | 11/2004 |
| JP | 200573985 A | 3/2005 |
| JP | 2005118238 A | 5/2005 |
| JP | 3112395 U | 8/2005 |
| JP | 2005323849 A | 11/2005 |
| JP | 2006168767 A | 6/2006 |
| JP | 2006168768 A | 6/2006 |
| JP | 2006168769 A | 6/2006 |
| JP | 200744159 A | 2/2007 |
| JP | 2007118987 A | 5/2007 |
| JP | 2007252828 A | 10/2007 |
| JP | 2007297065 A | 11/2007 |
| JP | 200867989 A | 3/2008 |
| JP | 2008105739 A | 5/2008 |
| JP | 2008125803 A | 6/2008 |
| JP | 2008264256 A | 11/2008 |
| JP | 3147037 U | 12/2008 |
| JP | 2008307237 A | 12/2008 |
| JP | 3149156 U | 3/2009 |
| JP | 3155666 U | 11/2009 |
| JP | 2010284438 A | 12/2010 |
| JP | 201172670 A | 4/2011 |
| WO | 9218178 A1 | 10/1992 |
| WO | 9729798 A1 | 8/1997 |
| WO | 9947062 A1 | 9/1999 |
| WO | 9962577 A1 | 12/1999 |
| WO | 0044422 A1 | 8/2000 |
| WO | 0100261 A1 | 1/2001 |
| WO | 0141666 A1 | 6/2001 |
| WO | 2007015469 A1 | 2/2007 |
| WO | 2009061315 A1 | 5/2009 |
| WO | 2009092430 A1 | 7/2009 |
| WO | 2009095701 A1 | 8/2009 |
| WO | 2010100104 A1 | 9/2010 |
| WO | 2010128328 A2 | 11/2010 |
| WO | 2010128406 A1 | 11/2010 |

* cited by examiner

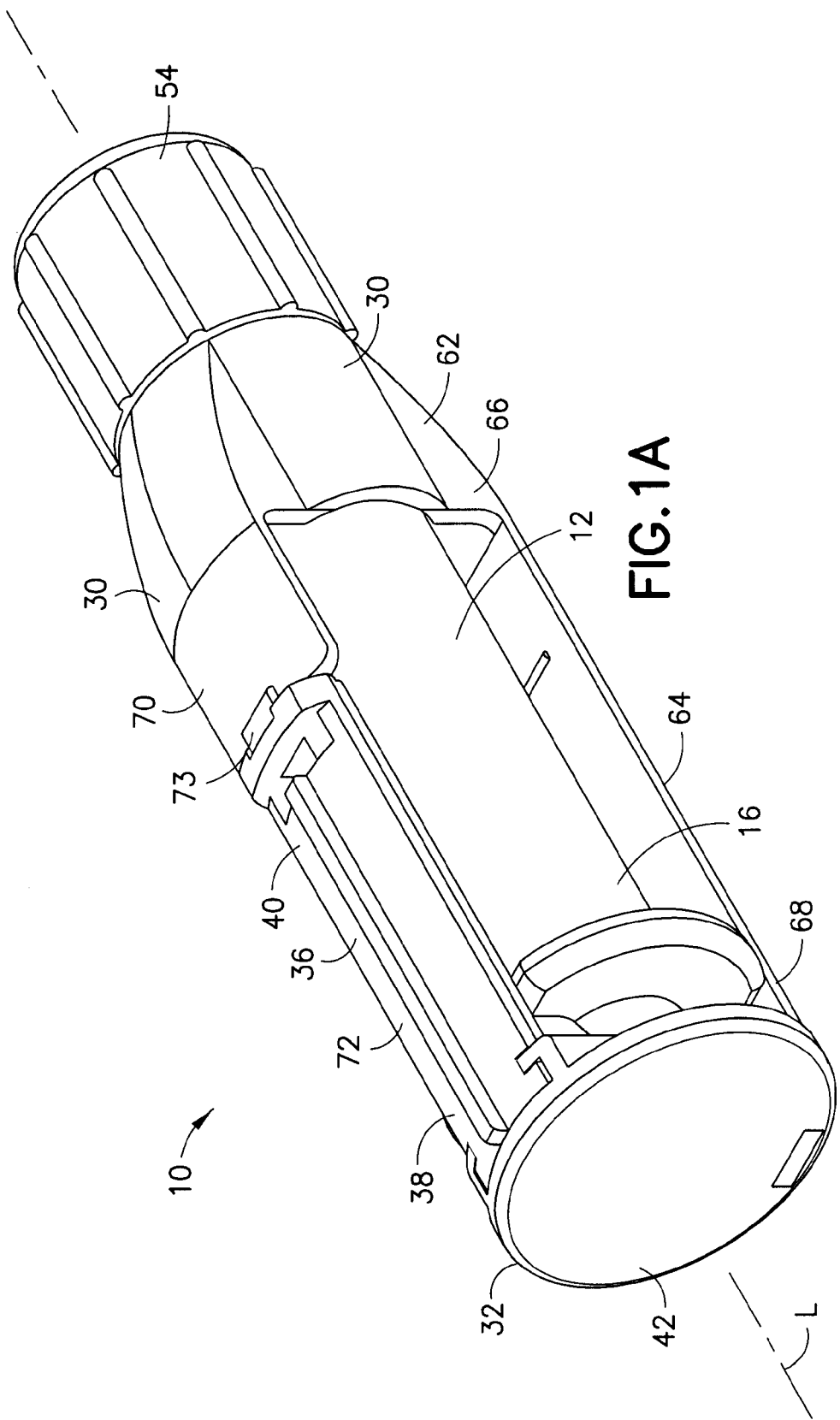

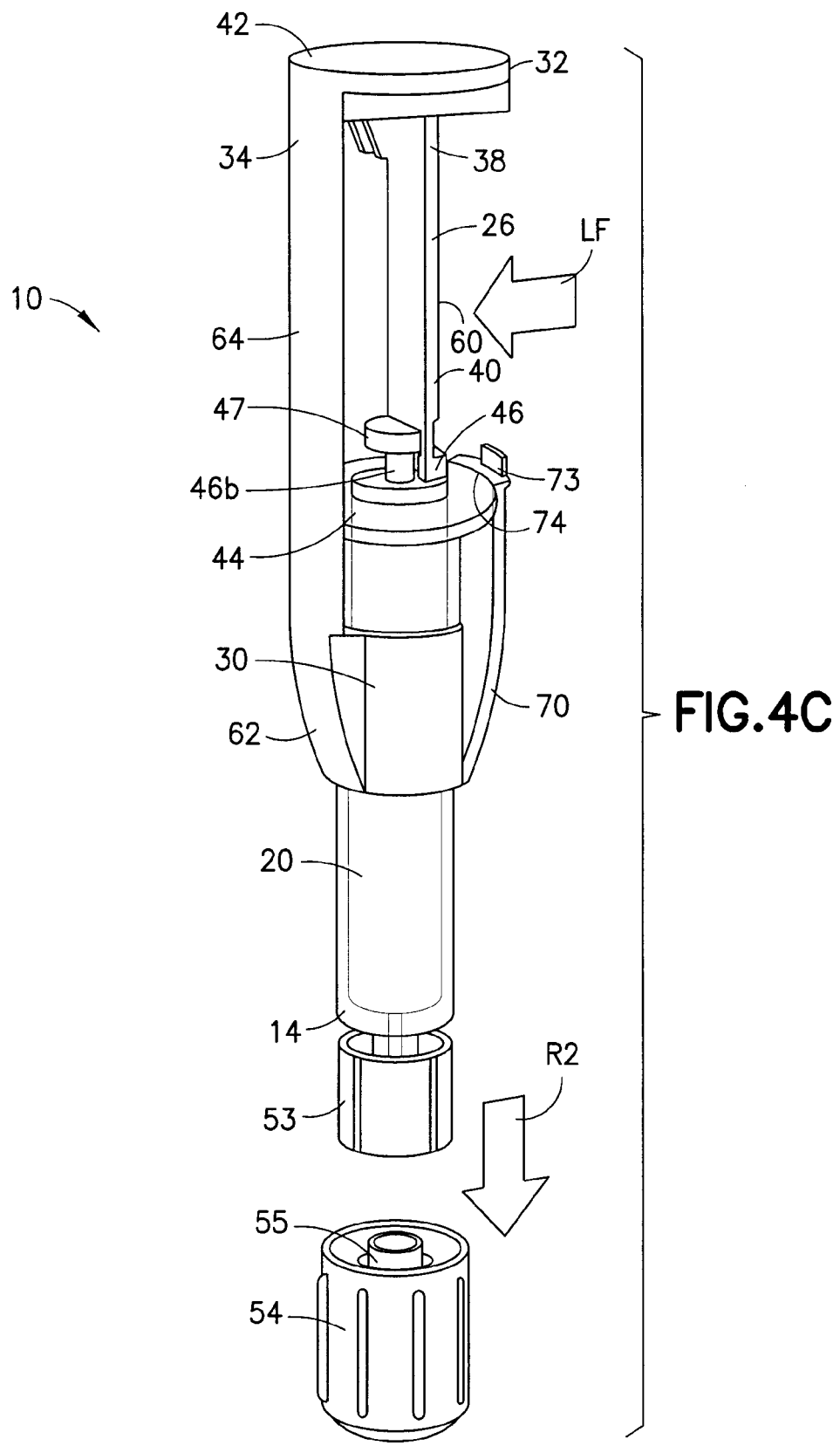

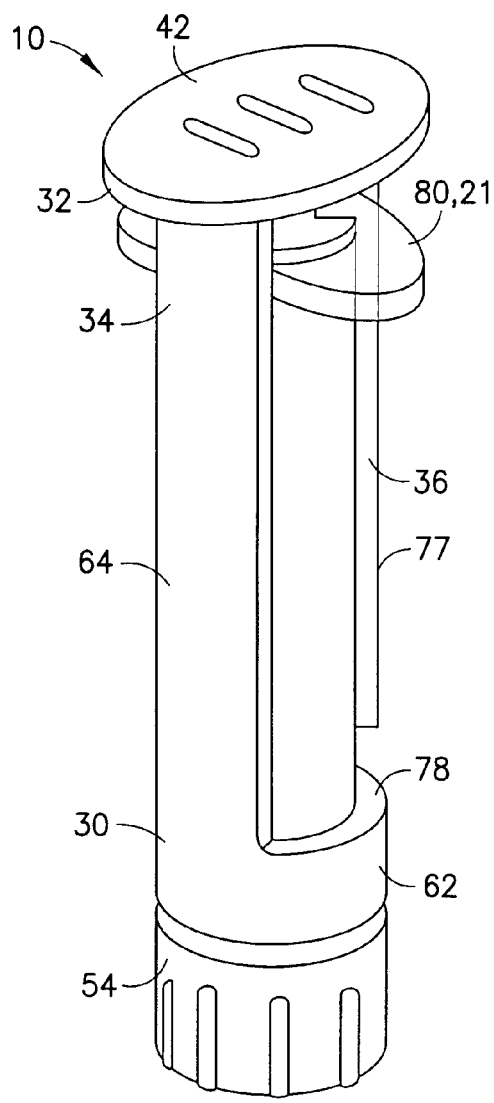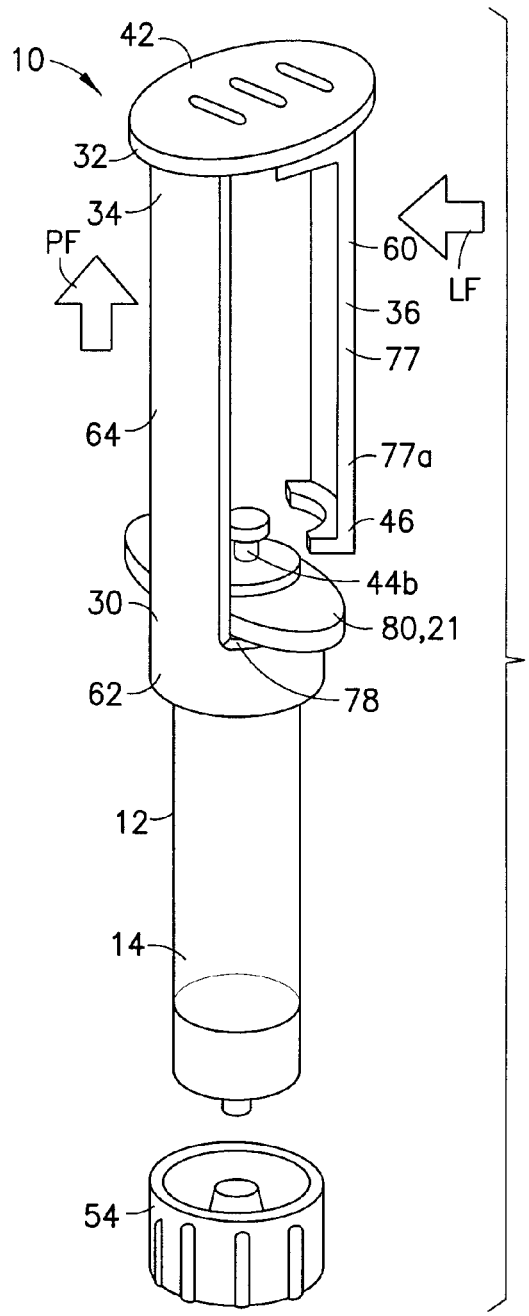
FIG.5A
FIG.5B

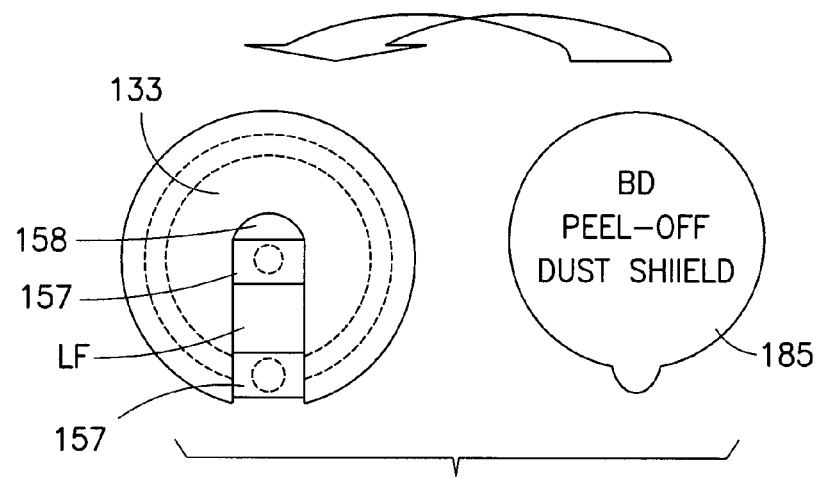
FIG.10
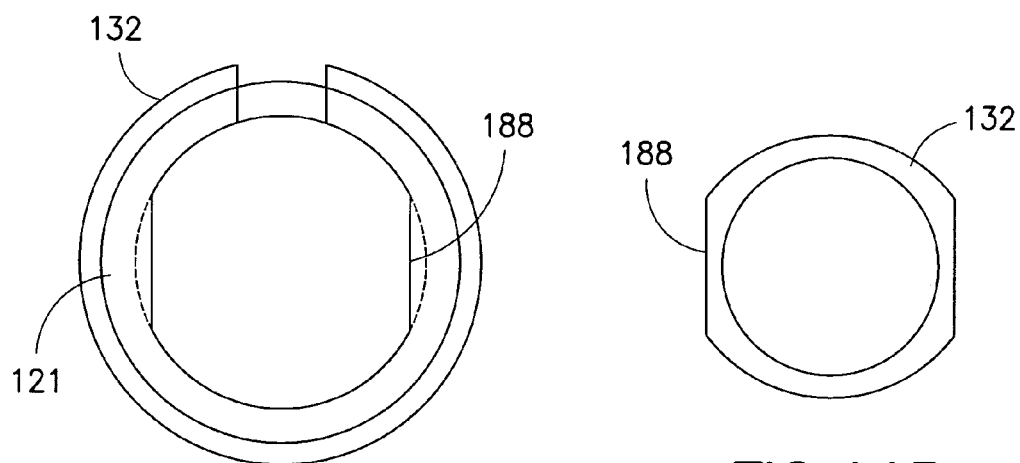
FIG.11A
FIG.11B

SPACE SAVING PLUNGER CAP AND ROD ASSEMBLY

CROSS-REFERENCE TO RELATED APPLICATION

This application claims priority to U.S. Provisional Patent Application Ser. No. 61/541,633 filed Sep. 30, 2011, the entire disclosure of which is hereby incorporated by reference.

BACKGROUND OF THE INVENTION

1. Field of the Invention

The present invention is directed to a syringe assembly including a space saving plunger cap and plunger rod assembly allowing for reduced storage space and more particularly, to a syringe assembly having a collapsed plunger rod which can be stored alongside a syringe barrel in a pre-use position which can subsequently be expanded and aligned with a stopper assembly into a ready-to-use position.

2. Description of Related Art

Syringe assemblies, and in particular hypodermic syringes, are well known in the medical field for dispensing fluids, such as medication. A conventional syringe typically includes a syringe barrel with an opening at one end and a plunger mechanism disposed through the other end. The plunger typically includes a plunger rod extending through the barrel, with a plunger head or stopper at the end of the plunger rod within the barrel and with a finger flange at the other end of the plunger rod extending out of the barrel. In use, the plunger rod is retracted through the syringe barrel to fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the front end of the syringe barrel for attachment with a fluid line of a patient. Upon depression of the plunger rod, the plunger rod and stopper travel through the syringe barrel, thereby forcing the contents of the syringe out through the opening at the front end for delivery to the patient. Such an operation is well known in the medical field, and medical practitioners have become well accustomed to the use of such common fluid delivery procedures through standard syringes.

Conventional syringes are well known to be used in connection with a vial of a medication, where the user draws the fluid into the syringe immediately prior to injection and delivery of the fluid to the patient. Oftentimes, hypodermic syringes may be packaged as "pre-filled" devices, wherein the syringe is pre-filled with medication prior to being packaged and delivered to the end user. In this manner, there is no need for the user to fill the device prior to injection, thereby saving time for the end user and maintaining consistent volumes for delivery.

Pre-filled syringes and pre-filled metered dose syringes are often filled with narcotics or other drugs at a production facility, packaged, and then shipped to a medical facility. Once at the facility, these syringes are often placed in controlled storage and/or locked cabinets to reduce theft of the syringes themselves and/or theft of the contents of these syringes. The space within these controlled storage locations is often limited, thus there is a need for a syringe assembly that has a smaller packaging footprint to reduce the storage space required for containing this syringe. It is also desirable to produce syringes that are uniform in terms of an outer surface shape to allow for stacking of the syringes within the storage cabinet.

SUMMARY OF THE INVENTION

In accordance with an embodiment of the present invention, a syringe assembly includes a syringe barrel having a first end, a second end, and a sidewall extending between the first and second ends defining a chamber. The syringe assembly also includes a stopper disposed within the chamber of the syringe barrel and a sleeve having a first end and a second end and extending at least partially about the syringe barrel. The syringe assembly further includes a cap associated with the second end of the sleeve, and a plunger rod having a first end and a second end with the first end of the plunger rod associated with the cap. The plunger rod is transitionable from a pre-use position, in which at least a portion of the second end of the plunger rod extends along a portion of the barrel sidewall, and a ready-to-use position in which the plunger rod is aligned with a stopper. Upon proximal movement of the sleeve in a direction away from the first end of the barrel, the plunger rod is configured for lateral movement with respect to the cap into the ready-to-use position.

The syringe assembly may also include a stopper adapter associated with the stopper, and the syringe barrel, stopper, and stopper adapter may be oriented along a longitudinal axis of the syringe assembly. The second end of the plunger rod may include an attachment member configured for cooperation with the stopper adapter. The first end of the plunger rod may include a slideable connection member for engaging a portion of the cap.

In certain configurations, the cap includes a radially extending track for cooperating with the slideable connection member of the plunger rod. In other configurations, the slideable connection member includes one of a male connection member and a female connection member and the track comprises the other of a cooperating male connection member and a cooperating female connection member. In still other configurations, at least a portion of the plunger rod moves along the track upon the application of a lateral force to a portion of the plunger rod.

The sleeve of the syringe assembly may include a distal portion which encompasses a portion of the syringe barrel and may also include at least one leg having a first end associated with the distal portion of the sleeve and a second end associated with the cap. The plunger rod may include a first portion associated with the distal portion of the sleeve and a stop, and a second portion associated with the cap. Upon proximal movement of the sleeve, the stop of the first portion cooperates with a syringe barrel flange to limit the proximal movement of the sleeve with respect to the syringe assembly. In other configurations, the distal portion of the sleeve includes a stop for cooperating with a radially extending flange of the syringe barrel to limit the proximal movement of the sleeve with respect to the syringe assembly.

Optionally, the slideable connection member includes a male connection member and the track includes a female groove extending through the cap for cooperating with the male connection member. At least a top portion of the male connection member may be accessible from a top surface of the cap so that the application of a lateral force to the top portion of the male connection member causes the plunger rod to move along the groove and into contact with the stopper. The syringe assembly may also include a removable dust shield positioned adjacent the top surface of the cap.

The syringe barrel may include an undercut flange portion and the cap may be rotatable about the syringe barrel during assembly to engage the cap with the undercut flange portion to prevent inadvertent actuation. The cap may be rotated about the syringe barrel to disengage the cap from the undercut flange portion prior to movement of the cap in a proximal direction. The syringe assembly may also include a stop member integral with the sleeve to limit proximal movement of the cap with respect to the syringe assembly. Optionally, the syringe assembly may include a liquid within the chamber. The syringe assembly may also include a tamper-indicating label disposed about a portion of the syringe assembly. The syringe assembly may also include a medication or drug disposed within the chamber of the syringe barrel.

In accordance with another embodiment of the present invention, a telescopic plunger rod and cap assembly for use with a syringe assembly includes a sleeve having a first end and a second end and configured for telescopic movement with respect to a syringe barrel. The assembly also includes a cap associated with the second end of the sleeve, and a plunger rod having a first end and a second end, with the first end associated with the cap. The plunger rod is transitionable from a pre-use position, in which at least a portion of the second end of the plunger rod is configured to extend along a portion of the barrel, to a ready-to-use position in which the plunger rod is aligned with a stopper, wherein upon relative movement of the sleeve with respect to the syringe barrel, the plunger rod is configured for lateral movement with respect to the cap into a ready-to-use position.

The second end of the plunger rod may include an attachment member configured for cooperation with the stopper, wherein the first end of the plunger rod includes a slideable connection member. The slideable connection member may include one of a male connection member and a female connection member and a track including the other of a cooperating male connection member and a cooperating female connection member. The sleeve may include a distal portion which encompasses a portion of the syringe barrel and at least one leg having a first end associated with the distal portion of the sleeve and a second end associated with the cap.

The plunger rod may include a first portion associated with the distal portion of the sleeve and including a stop, and a second portion associated with the cap. Upon proximal movement of the sleeve with respect to the syringe barrel, the stop of the first portion cooperates with a syringe barrel flange to limit the proximal movement of the sleeve with respect to the syringe assembly. The distal portion of the sleeve may include a stop surface for cooperating with a syringe barrel flange to limit the proximal movement of the sleeve with respect to the syringe assembly.

In accordance with another embodiment, a syringe assembly includes a syringe barrel having a proximal end, a distal end, and a sidewall extending between the proximal and distal ends defining a chamber. The syringe assembly also includes a stopper disposed within the chamber of the syringe barrel, and a sleeve at least partially disposed about the syringe barrel. The syringe assembly further includes a plunger rod having a first end and a second end, with both the first end and the second end being integral with the sleeve in a first pre-use position and one of the first end and the second end being laterally advanceable with respect to a portion of the sleeve to integrally engage the stopper in a second ready-to-use position.

In certain configurations, the plunger rod moves from the first position to the second position upon proximal movement of the sleeve with respect to the barrel. In other configurations, the plunger rod is movable in a lateral direction with respect to a longitudinal axis of the sleeve upon proximal movement of the sleeve with respect to the barrel. The syringe assembly may also include a stopper adapter associated with the stopper, wherein one of the first end and second end of the plunger rod includes an attachment member configured for cooperation with the stopper adapter when the stopper is in the second position.

BRIEF DESCRIPTION OF THE DRAWINGS

FIG. 1A is a front perspective view of a space saving syringe assembly with a plunger rod in a collapsed position in accordance with an embodiment of the present invention.

FIGS. 4A-4D are perspective side views of the syringe assembly of FIGS. 1A-1C and 2A-2C illustrating the sequential operational steps for moving the plunger rod from the collapsed pre-use position to the expanded ready-to-use position in accordance with an embodiment of the present invention.

FIG. 5A is a perspective view of a syringe assembly wherein the plunger rod is in the collapsed position, in accordance with an embodiment of the present invention.

FIG. 5B is a perspective view of the syringe assembly of FIG. 5A wherein the plunger rod is in the expanded position in accordance with an embodiment of the present invention.

FIG. 10 is a top view of the syringe assembly of FIGS. 6A-6C including the direction of movement of the syringe assembly into the ready-to-use position and a dust shield used during shipping in accordance with an embodiment of the present invention.

FIG. 11A is a bottom view of the plunger cap of FIGS. 6A-6C in accordance with an embodiment of the present invention.

FIG. 11B is a partial top view of the syringe assembly of FIGS. 6A-6C in accordance with an embodiment of the present invention.

DESCRIPTION OF THE PREFERRED EMBODIMENTS

Figure 1B:
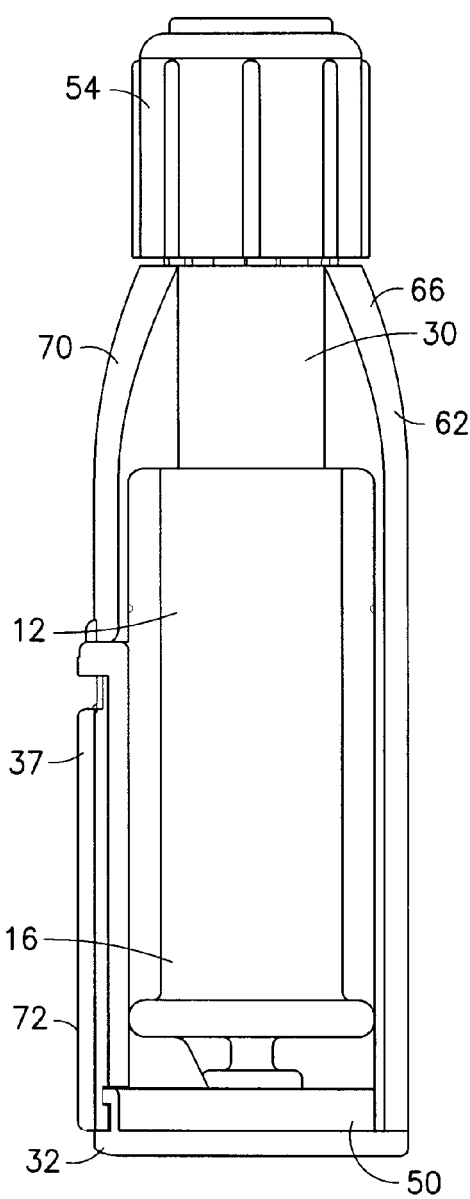
FIG. 1B is a side view of the syringe assembly of FIG. 1A in accordance with an embodiment of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Reference is now made to FIGS. 1A-1C, 2A-2C, 3, 4A-4D, and 5A-5B which depict a syringe assembly according to an embodiment of the invention, generally indicated as 10, adapted for the dispensing and delivery of a fluid. FIGS. 6A-6C, 7A-7C, 8A-8C, and 9A-9C depict a syringe assembly according to a further embodiment of the invention, generally indicated as 100, which can also be adapted for the dispensing and delivery of a fluid.

With particular reference to FIGS. 1A-1C, 2A-2C, and 3, the syringe assembly 10 is intended for use for injection or infusion of fluid, such as a medication, directly into a patient, and is generally shown and described for purposes of the present description as a hypodermic syringe. Syringe assembly 10 is contemplated for use in connection with a needle such as by connecting syringe assembly 10 to a separate needle assembly (not shown), or alternatively for connection with a separate intravenous (IV) connection assembly (not shown).

The syringe assembly 10 includes a syringe barrel 12 having a first or distal end 14, a second or proximal end 16, and a sidewall 18 extending between the distal end 14 and proximal end 16 defining an interior chamber 20 of the syringe barrel 12. A stopper 22 is slideably disposed within the chamber 20 of the syringe barrel 12. The syringe barrel 12 may be in the general form of an elongated cylindrical barrel as is known in the art for the general shape of a hypodermic syringe, although other forms for containing a fluid for delivery are also contemplated by the present invention. Additionally, the syringe barrel 12 may be formed of glass, or may be injection molded from thermoplastic material such as polypropylene and polyethylene according to techniques known to those of ordinary skill in the art, though it is to be appreciated that the syringe barrel 12 may be made from other suitable materials and according to other applicable techniques. In certain configurations, the syringe barrel 12 may include an outwardly extending flange 21 about at least a portion of the proximal end 16. The flange 21 may be configured for easy grasping by a medical practitioner, as will be discussed herein.

Figure 3:
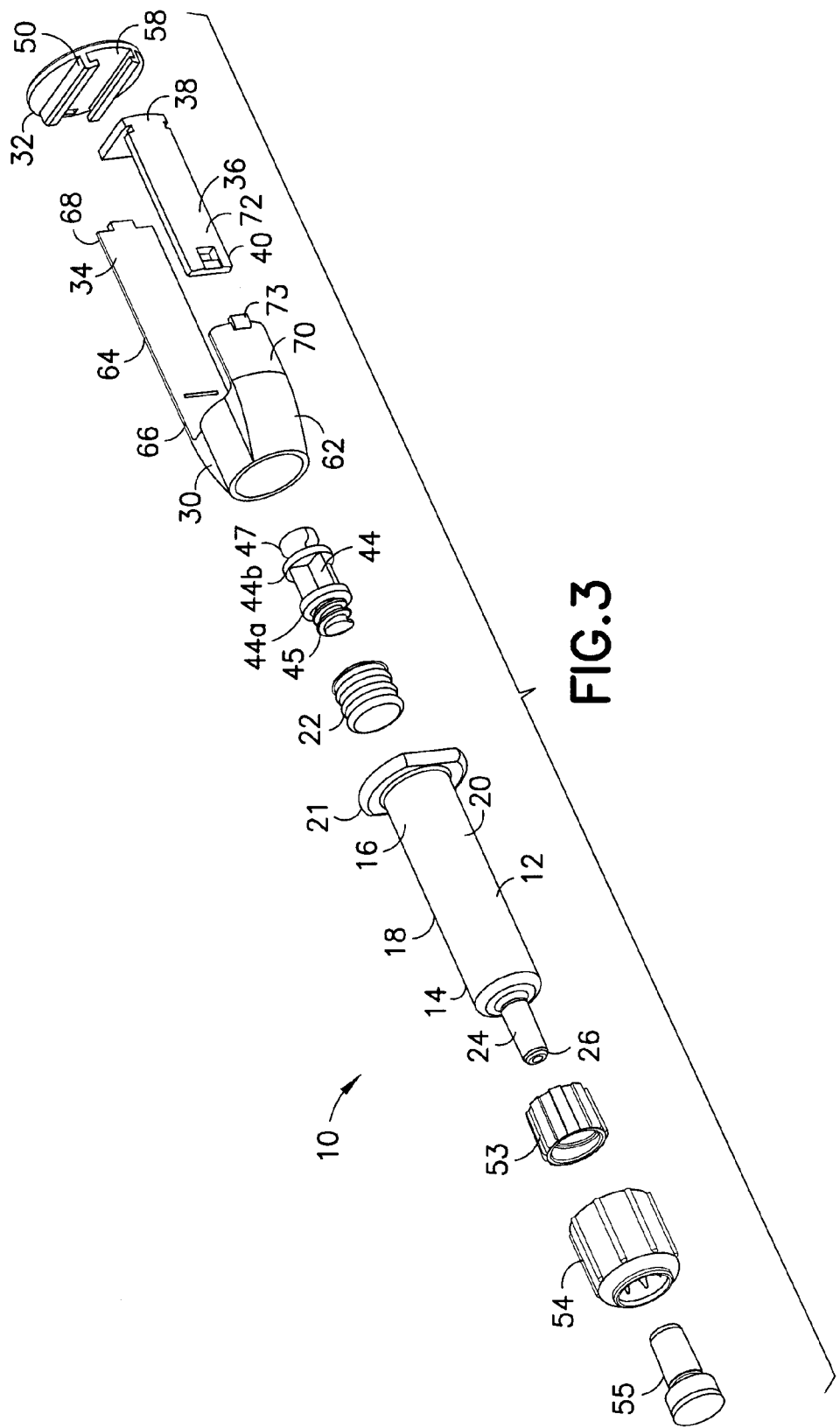
FIG. 3 is an expanded perspective view of the syringe assembly of FIG. 1A in accordance with an embodiment of the present invention.

As illustrated in FIG. 3, the distal end 14 of the syringe barrel 12 terminates in a tip 24 having an outlet opening 26. The proximal end 16 is generally open-ended, but is intended to be closed off to the external environment, via the stopper 22, as will be discussed herein. According to one non-limiting embodiment, as shown in FIG. 3, the syringe assembly 10 can include a tip cap 54, an interface member 53 interfacing between the tip cap 54 and the tip 24 of the syringe barrel 12, and a plug 55, for sealing the outlet opening 26.

The syringe barrel 12 may include markings, such as graduations on the sidewall 18 thereof, for providing an indication as to the level or amount of fluid contained within the syringe barrel 12. Such markings may be provided on the external wall, the internal wall, or integrally formed or otherwise within the wall of syringe barrel 12. Alternatively, or in addition thereto, the markings may provide a description of the contents of the syringe, or other identifying information, as may be known in the art.

As noted, distal end 14 of syringe barrel 12 includes an outlet opening 26. The profile of outlet opening 26 may be adapted for engagement with a separate dispensing device, such as a needle assembly or IV connection assembly, and therefore may include a mechanism for such engagement, for example, a generally tapered luer tip, for engagement with a separate tapered luer mating surface (not shown) of such a separate device for attachment therewith. In addition, a mechanism for locking engagement therebetween may also be provided, such as a luer collar or luer lock including interior threads. Such luer connections and luer locking mechanisms are well known in the art.

All of the components of syringe assembly 10 may be constructed of any known material, and are desirably constructed of medical grade polymers. As stated above, the syringe assembly 10 is particularly useful as a pre-filled syringe, and therefore may be provided for end use with a fluid, such as a medication, contained within interior chamber 20 of syringe barrel 12, pre-filled by the manufacturer. In this manner, syringe assembly 10 can be manufactured, pre-filled with a medication, sterilized, and packaged in appropriate packaging for delivery, storage, and use by the end user, without the need for the end user to fill the syringe with medication from a separate vial prior to use.

With continuing reference to FIGS. 1A-1C, 2A-2C, 3, 4A-4D, and 5A-5B, the syringe assembly may include a sleeve 30 at least partially disposed about the syringe barrel 12. A cap 32 is associated with a proximal end 34 of the sleeve 30. The sleeve 30 further includes a plunger rod 36 having a first end 38 and a second end 40 associated with the cap 32 by connection with the first end 38. The plunger rod can have any configuration known in the art including a star shape, multiple lobe, or flat rod design. The first end 38 of the plunger rod 36 is associated with the cap 32 and is configured for cooperation with the cap 32 and the sleeve such that in a pre-use position, at least a portion of the second end 40 of the plunger rod 36 extends along a portion of the barrel sidewall 18.

Figure 4A:
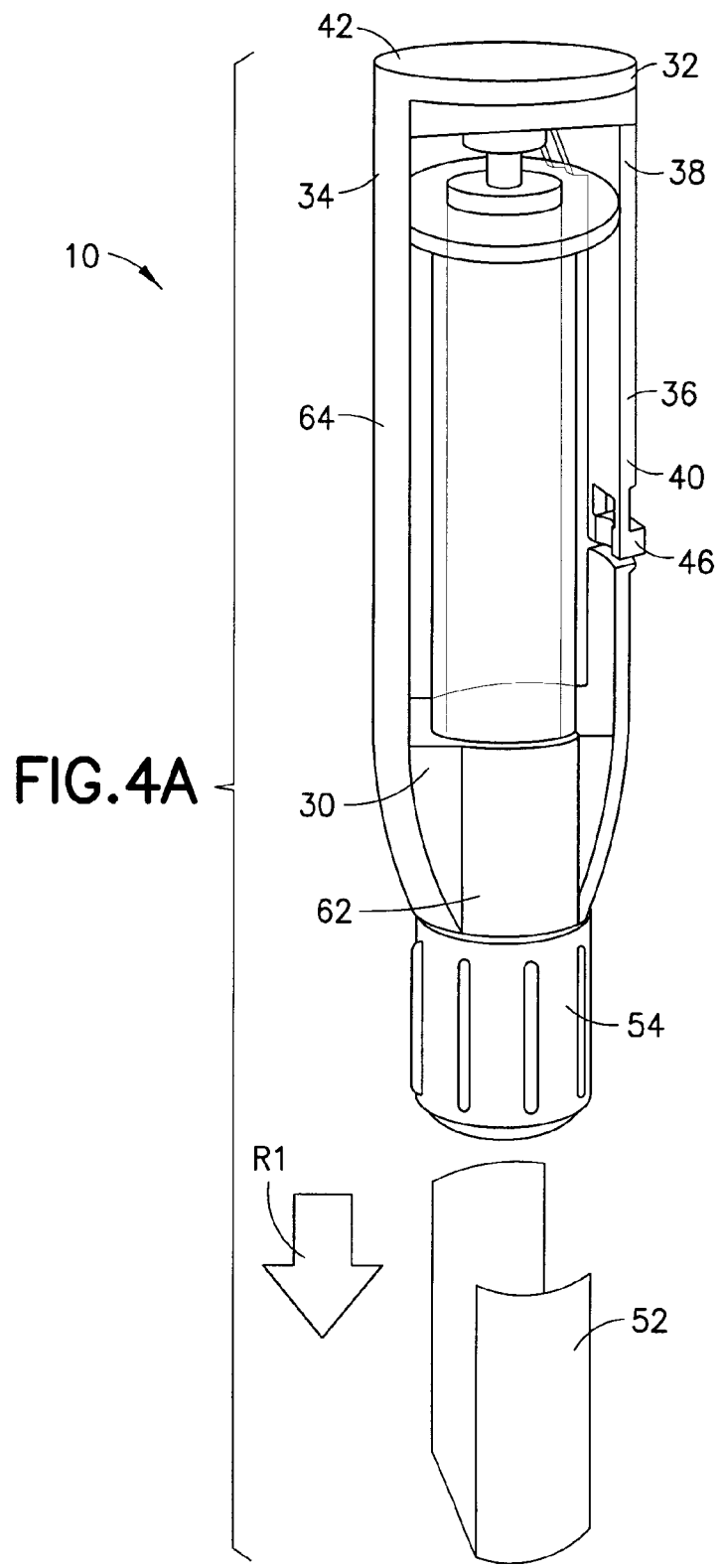

In order to operate the syringe assembly and to position the plunger rod 36 into a ready-to-use position, reference is made to FIGS. 4A-4D. FIG. 4A shows removal R1 of a protective packaging member or tamper indicating label 52, to be described in more detail below. Once the protective member 52 is removed, a proximal force PF, shown in FIG. 4B, can be applied to the sleeve 30 in order to cause the sleeve to move a predetermined distance in the proximal direction with respect to the barrel 12. Once the sleeve 30 has been moved a sufficient amount so that the portion of the sleeve 30 defining the plunger rod 36 is advanced proximally of the syringe barrel 12, the plunger rod 36 can be laterally moved via a lateral force, such as a force applied by hand, as shown by LF in FIG. 4C. This lateral force LF causes plunger rod 36 to move with respect to the cap 32 into a ready-to-use position in which the plunger rod 36 is aligned with the stopper 22. It can be appreciated that the proximal force PF applied to the sleeve 30 can be in any direction, either toward the user or away from the user, as long as this force draws the sleeve 30 in a proximal direction away from the distal end 14 of the syringe barrel 12. It also can be appreciated that the plunger rod 36 can be aligned in any manner with the stopper 22 and is not limited to just an alignment along the longitudinal axis of the stopper 22. The tip cap 54 can be moved as shown by R2 in FIG. 4C to prepare the syringe assembly 10 for use. The interaction between the cap 32 and the plunger rod 36 is described in more detail below.

Figure 4B:
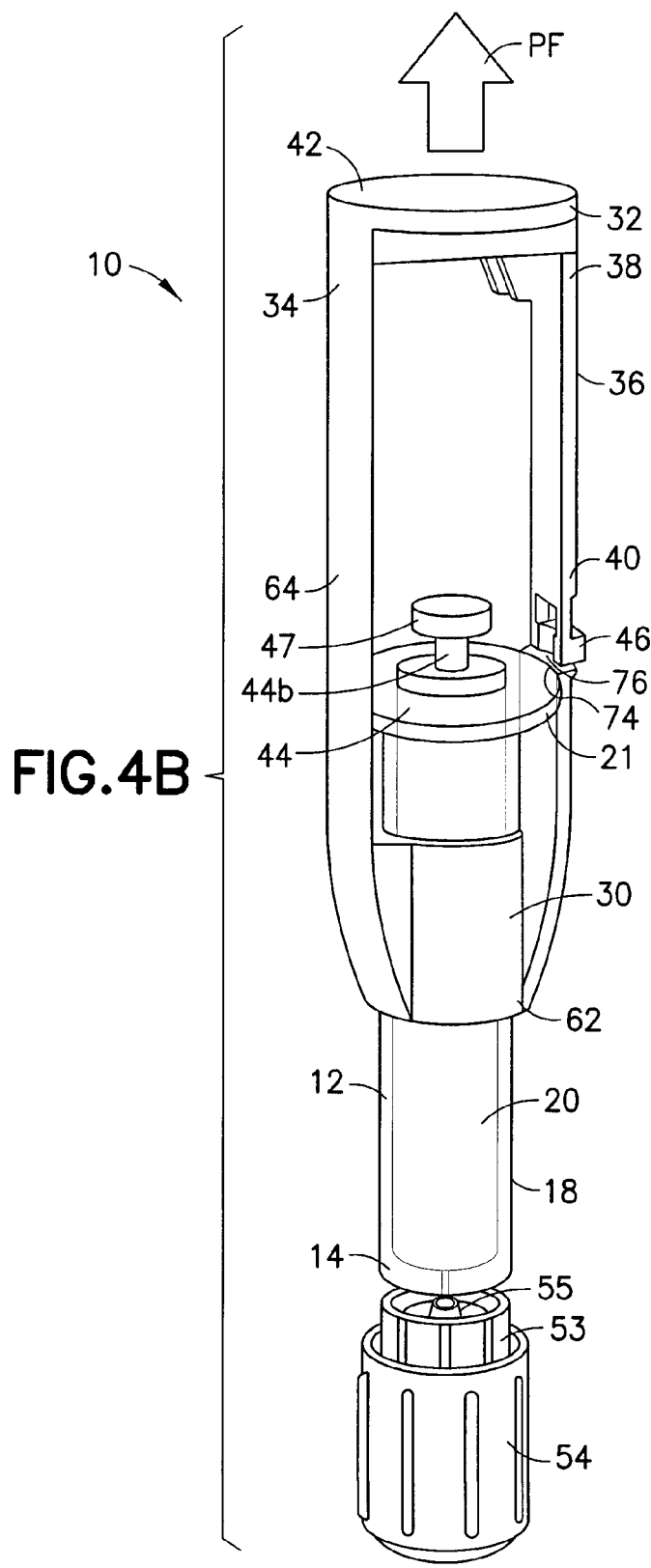
Figure 4D:
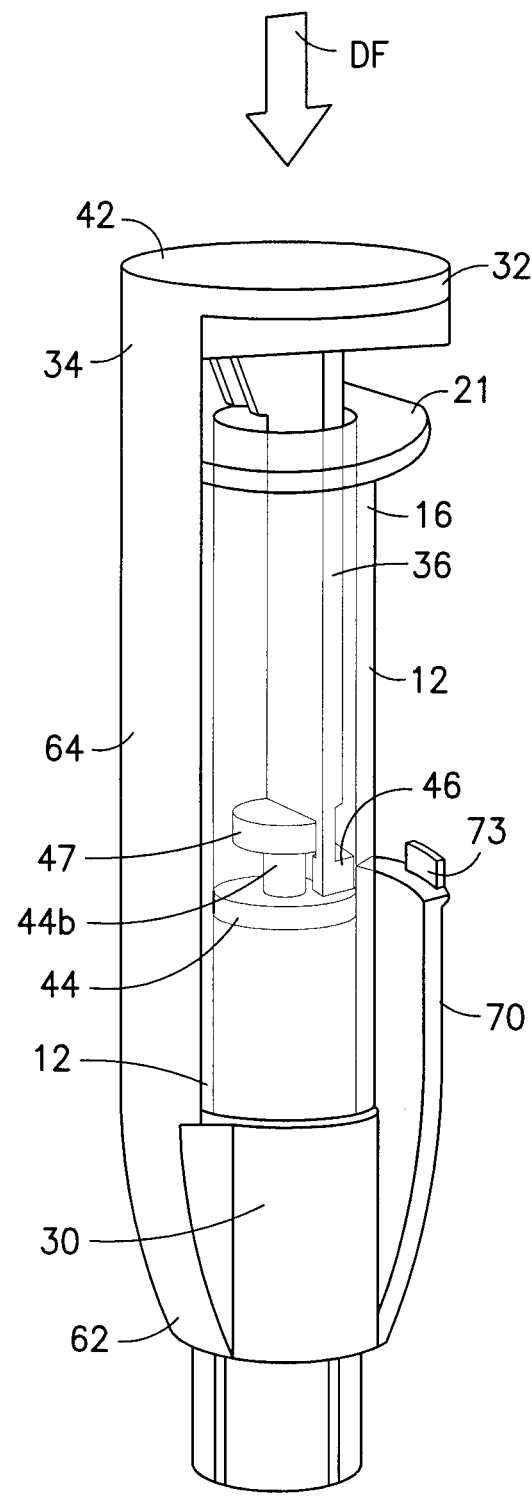

The cap 32 can include a thumb press portion 42, or any other type of well-known member, upon which a user can apply a distally directed force DF as shown in FIG. 4D, to cause the plunger rod 36 to move the stopper 22, disposed within the syringe barrel 12, toward the distal end 14 of the syringe barrel 12 to expel the syringe contents during operation of the syringe assembly 10.

Figure 2B:
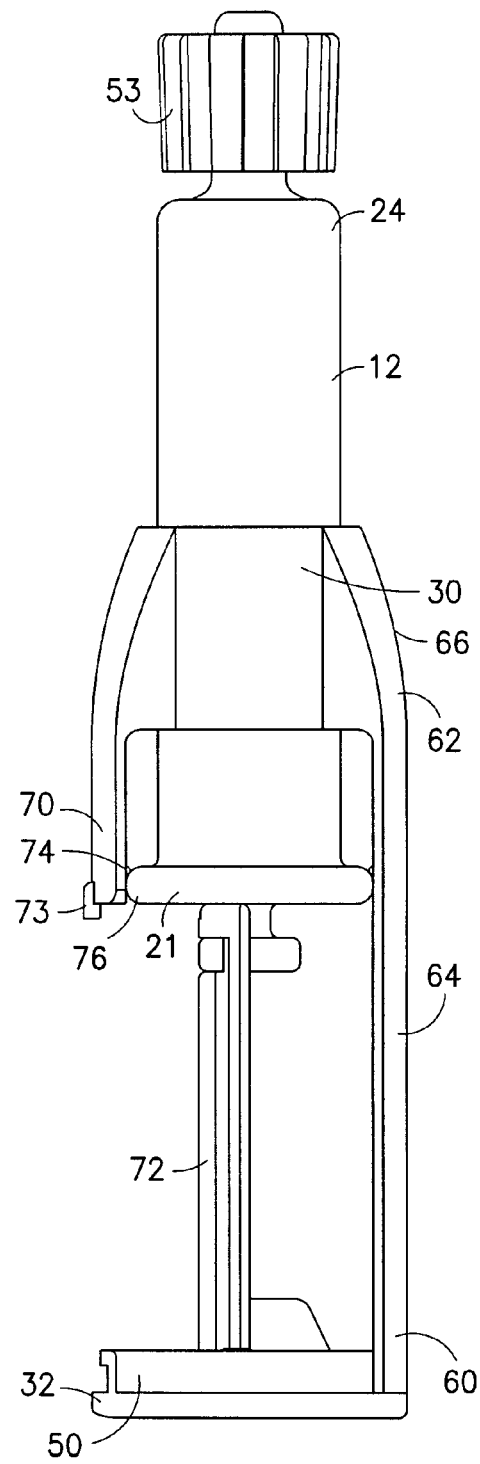
FIG. 2B is a side view of the syringe assembly of FIG. 2A in accordance with an embodiment of the present invention.
Figure 1C:
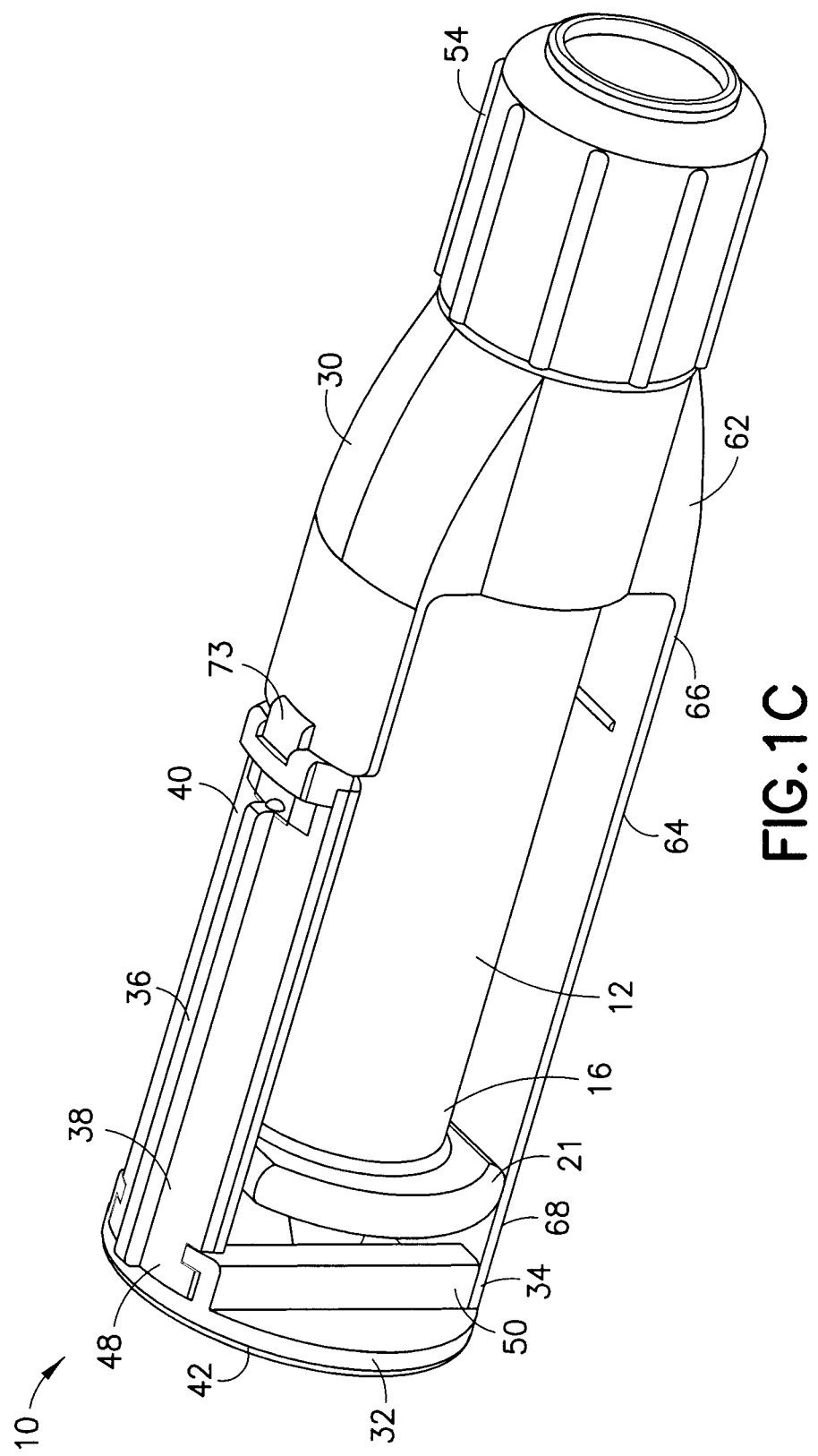
FIG. 1C is a rear perspective view of the syringe assembly of FIG. 1A in accordance with an embodiment of the present invention.
Figure 2A:
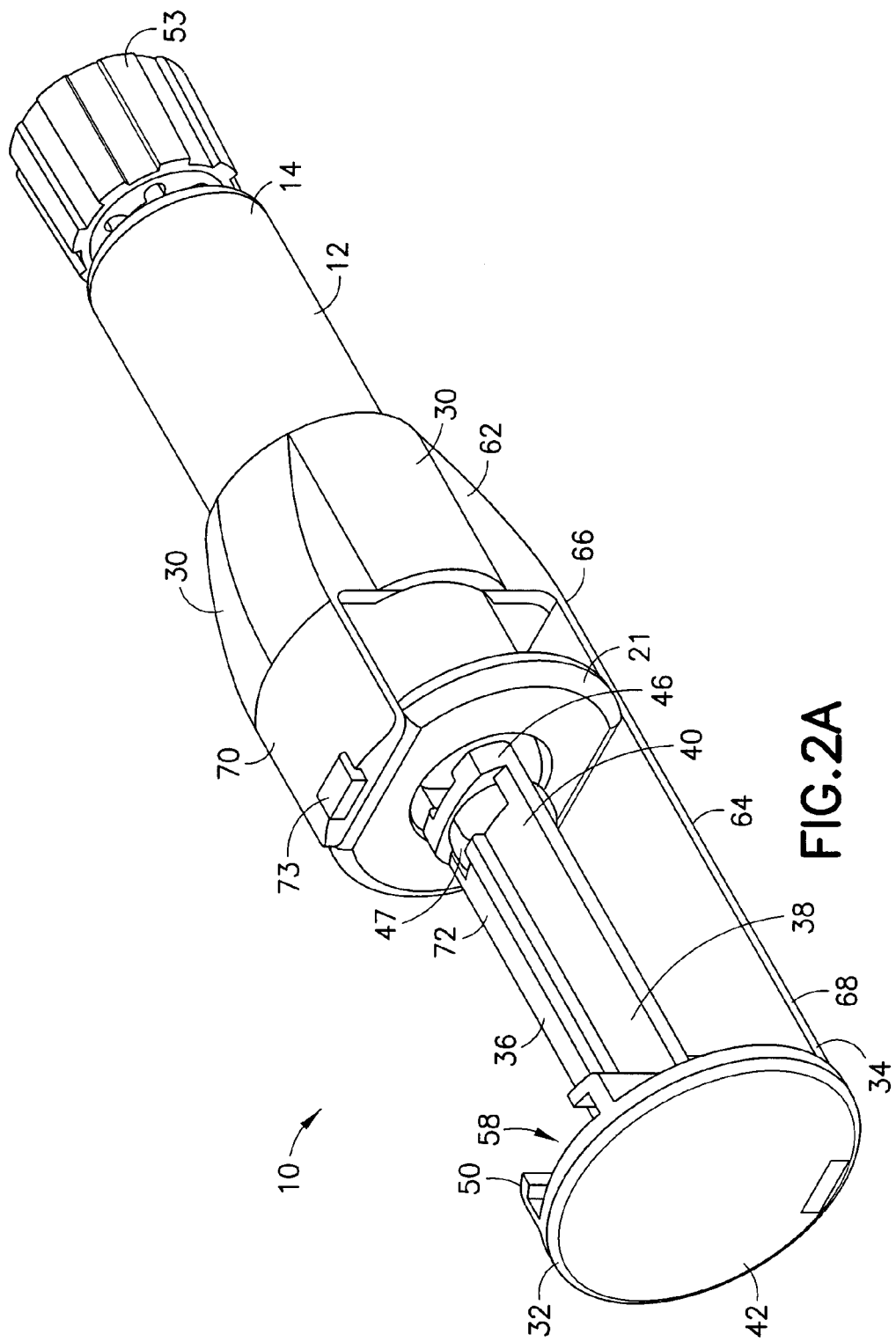
FIG. 2A is a front perspective view of the space saving syringe assembly of FIG. 1A with the plunger rod in an expanded position in accordance with an embodiment of the present invention.
Figure 2C:
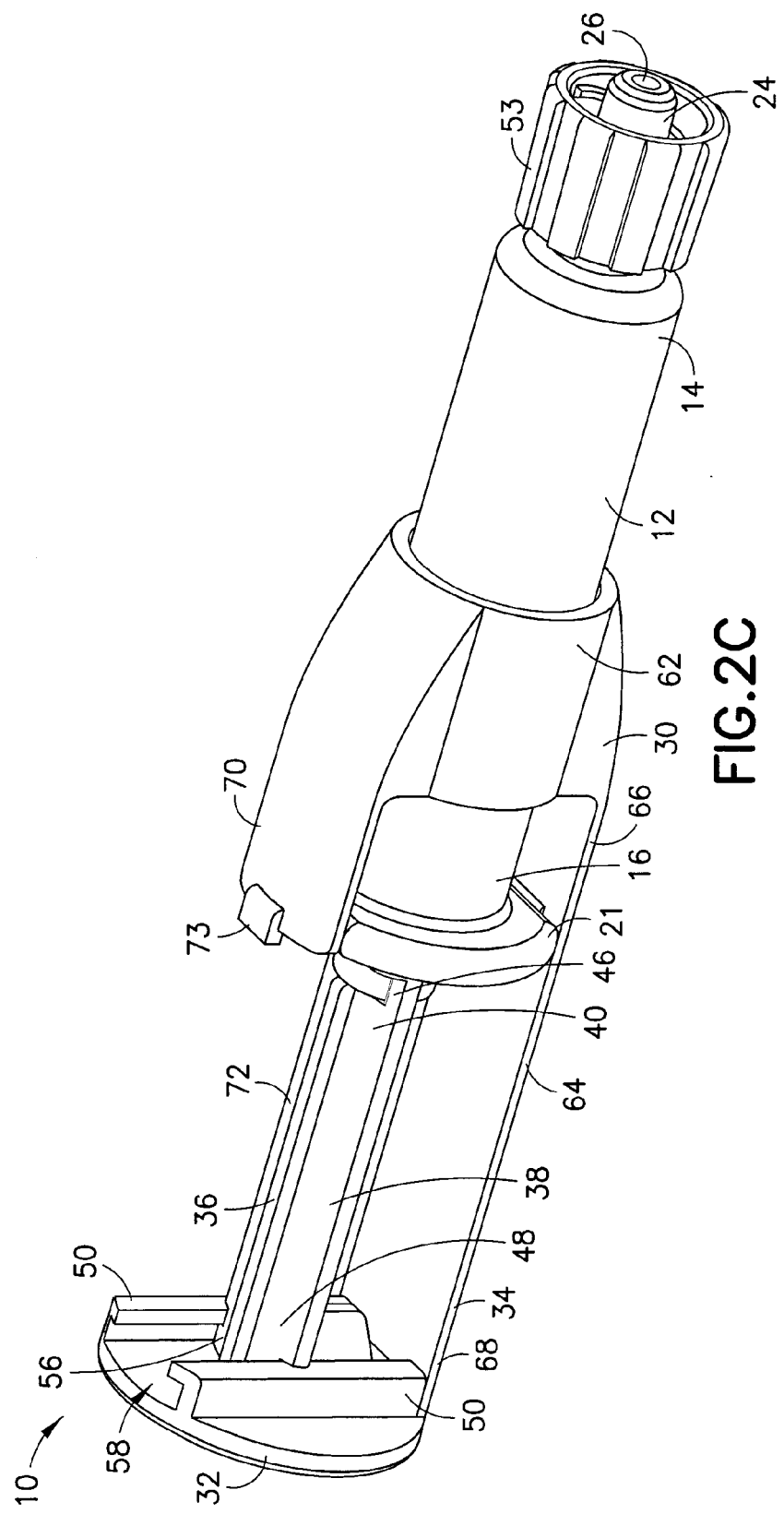
FIG. 2C is a back perspective view of the syringe assembly of FIG. 2A in accordance with an embodiment of the present invention.

Reference is now made to FIG. 3 which shows a stopper adapter 44 associated with the stopper 22 wherein the syringe barrel 12, stopper 22, and stopper adapter 44 are aligned along a longitudinal axis L, as shown in FIG. 1A. The stopper adapter 44 acts as an interface between the stopper 22 and the plunger rod 36. According to one embodiment, the syringe barrel 12, stopper 22, and stopper adapter 44 can define a longitudinal axis, however, it can be appreciated that the syringe barrel 12, stopper 22, and stopper adapter 44 can be aligned in another manner as long as these components are aligned to ensure cooperating movement with one another. The stopper adapter 44 can include a first end 44a and a second end 44b. The first end 44a of the stopper adapter 44 may be configured for mating engagement with a corresponding portion of the stopper 22. This mating can occur by any well known means, such as a threaded engagement 45, as shown in FIG. 3, friction fit, male/female interaction, and the like. The second end 44b of the stopper adapter 44 can be configured to mate with the second end 40 of the plunger rod 36. According to one design, the second end 40 of the plunger rod 36 can include an attachment member 46, as shown in FIGS. 2A and 2C, such as in the form of a female clip member which is configured to mate with a male connection member 47 located at the second end 44b of the stopper adapter 44. It can be appreciated that other forms or designs may be contemplated for the attachment member 46 and the connection member 47 as long as this design results in a secure mating of these members.

As best shown in FIG. 2C, according to one embodiment, the first end 38 of the plunger rod 36 can include a slideable connection member 48 and the cap 32 can include a radially extending track 50 for cooperating with the slideable connection member 48 of the plunger rod 36.

With continuing reference to FIGS. 1A-1C, 2A-2C, 3, 4A-4D, and 5A-5B, the slideable connection member 48 can include a male connection member 56 and the track 50 can include a female groove 58 configured for cooperating with the male connection member 56. Although FIGS. 1A-1C, 2A-2C, 3, 4A-4D, and 5A-5B show a male connection member 56 cooperating with a female groove 58 located in track 50, it can be appreciated that the slideable connection member 48 can comprise either a male connection member or a female connection member and the track 50 can comprise the other of a cooperating male connection member and a cooperating female connection member. Upon the application of lateral force LF to a side portion 60 of the plunger rod 36, as discussed above and shown in FIGS. 4C and 5B, the plunger rod 36 moves along the track 50 into longitudinal alignment with the stopper 22 and into the ready-to-use position.

In accordance with an embodiment of the present invention, the sleeve 30 can include a distal portion 62 which extends at least partially about a portion of the syringe barrel 12 and at least one leg 64 having a first end 66 associated with the distal portion 62 of the sleeve 30 and a second end 68 associated with the cap 32. According to one design, shown in FIGS. 1A-1C, 2A-2C, 3, and 4A-4D, the sleeve also includes plunger rod 36 connected to the cap 32, such as on opposing sides of the cap 32, as shown in FIG. 1A. In one embodiment, plunger rod 36 has a first end 38 and a second end 40 wherein both the first end 38 and the second end 40 are integral with the sleeve 30 in a first pre-use position and one of the first end 38 and the second end 40 are integral with the stopper 22 or stopper adapter 44 in a second ready-to-use position. In particular, the plunger rod 36 can include a first portion 70 and a second portion 72 which are removably secured together via a clip 73 or any other known type of connection member. In this design, the first portion 70 is associated with the distal portion 62 of the sleeve 30 and can include a stop 74, as best shown in FIGS. 4B and 4C, configured for cooperation with the stopper adapter 44 or a portion of the syringe barrel 12, such as the barrel flange 21 upon proximal movement of the sleeve 30, as described below, and the second portion 72 is associated with the cap 32. Upon proximal movement of the sleeve 30, as shown in FIG. 4B, the stop 74 of the first portion 70 cooperates with a portion 76 of the barrel flange 21, which can be the flange portion of the syringe barrel 12, as shown in FIG. 2B or the stopper adapter 44, to limit the proximal movement of the sleeve 30 with respect to the syringe assembly 10. Once proximal movement of the sleeve 30 is completed and the second portion 72 of the plunger rod 36 has cleared the syringe barrel 12 such that it is no longer positioned alongside the syringe barrel 12, this second portion 72 can be moved along the track 50 and mated with the stopper adapter 44, as described above, into the ready-to-use position.

Reference is now made to FIGS. 5A-5B which show another embodiment of the syringe assembly 10. In this design, the plunger rod 36 includes a single leg 77 that terminates at one end 77a with the attachment member 46 which is configured for mating with the second end 44b of the adapter 44. In contrast to the first design, described above and shown in FIGS. 1A-1C, 2A-2C, 3, and 4A-4D, leg 77, as shown in FIGS. 5A-5B, is not connected to or associated with the distal portion 62 of the sleeve 30. However, the sleeve 30 does include leg 64 which extends between and is connected to the cap 32 and the distal portion 62 of the sleeve. The distal portion 62 of the sleeve 30 can include a stop surface 78, such as a top portion of the distal portion 62. This stop surface 78 is configured for cooperating with a flange, such as the flange 21 of the syringe barrel or a separate flange 80, which can be associated with the second end 44b of the stopper adapter 44, to limit the proximal movement of the sleeve 30 with respect to the syringe assembly 10. It can be appreciated that flange 21, 80 may have any type of laterally extending portion configured to contact the stop surface 78 of the distal portion 62 of the sleeve 30 upon proximal movement of the sleeve 30 away from the distal end 14 of the syringe barrel 12. In operation, a proximal force PF as shown in FIG. 5B is applied to the sleeve 30 to move sleeve 30 and the plunger rod 36 away from the distal end 14 of the syringe barrel 12 an amount sufficient for the plunger rod 36 to clear the sidewall 18 of the syringe barrel 12. Once this clearance is achieved, the plunger rod 36 can be moved in a lateral direction with respect to the cap 32, stopper 22, and stopper adapter 44, by the application of a lateral force LF, and mated with the stopper adapter 44, as discussed in detail above, in order to position the plunger rod 36 in the ready-to-use position.

As discussed above, the syringe assembly 10 can be a pre-filled syringe assembly 10. A tamper indicating label 52, as shown in FIG. 4A, can be positioned about a tip cap 54 and a portion of the sleeve 30. It can be appreciated that the tamper indicating label 52 can be of a design known in the art and can include a frangible or perforated portion for ease of removal from the syringe assembly 10. This frangible portion can include markings, as known in the art, to indicate if any tampering has occurred. One type of label is a shrink-wrap type label which can encompass the tip cap 54 and a portion of the sleeve 30 in order to prevent unintentional proximal movement of the sleeve 30, as discussed above, until the operator is ready to use the syringe assembly.

Reference is now made to FIGS. 6A-6C, 7A-7C, 8A-8C, and 9A-9C which show perspective, side elevation, and cross-sectional views of the syringe assembly, generally indicated as 100, at various stages of actuation, according to a second embodiment of the invention. The syringe assembly 100 is similar to syringe assembly 10, as discussed in detail above and includes a first or distal end 114, a second or proximal end 116, and a sidewall 118 extending between the distal end 114 and proximal end 116 defining an interior chamber 120 of a syringe barrel 112. A stopper 122 is disposed within the chamber 120 of the syringe barrel 112. The syringe barrel 112 may include an outwardly extending flange 121 about at least a portion of the proximal end 116. The flange 121 may be configured for easy grasping by a medical practitioner.

Figure 6A:
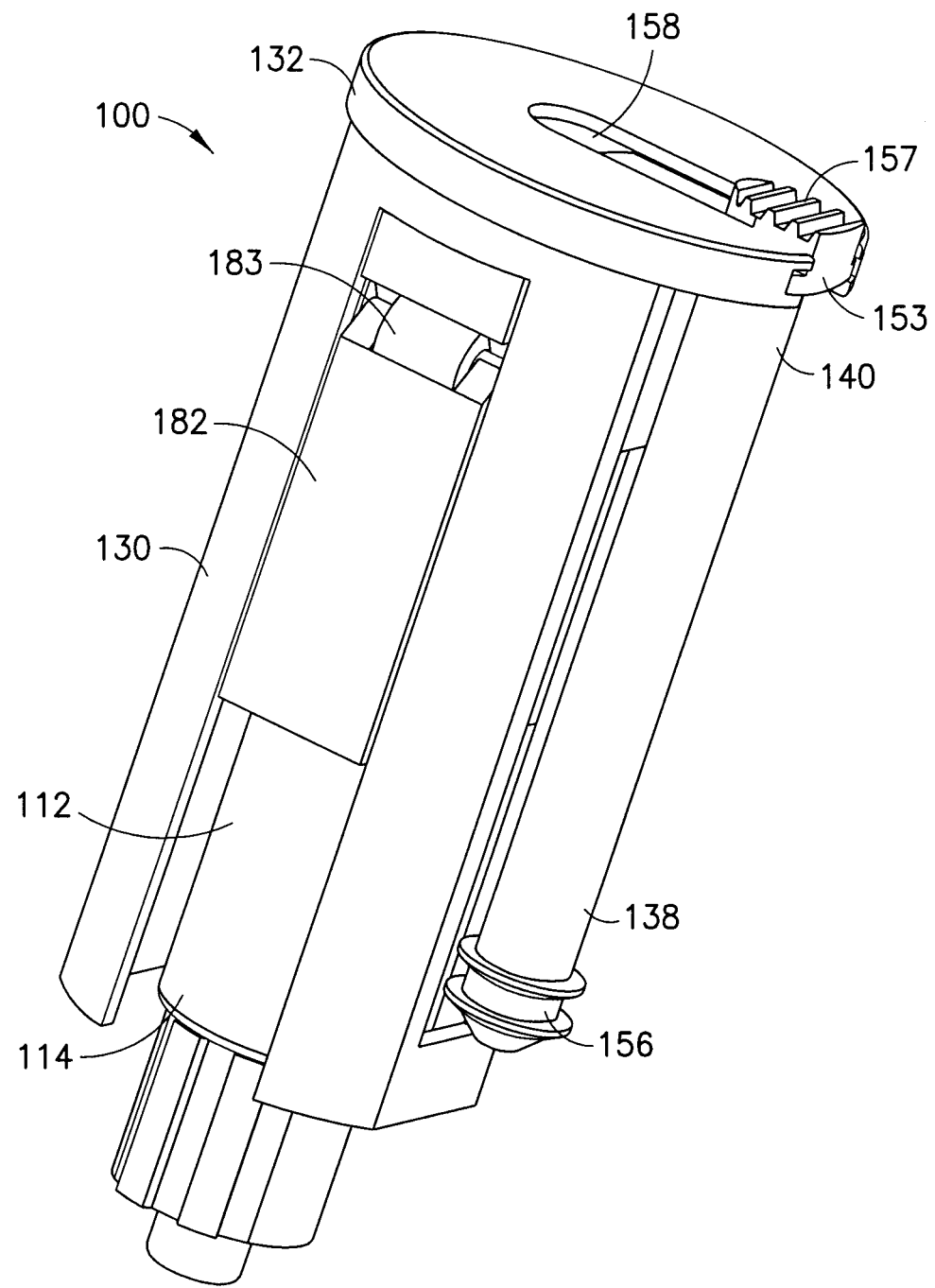
FIGS. 6A-6C are perspective, side elevation, and cross-sectional views of the syringe assembly with the plunger rod and sleeve in a collapsed, pre-use position in accordance with an embodiment of the present invention.
Figure 6B:
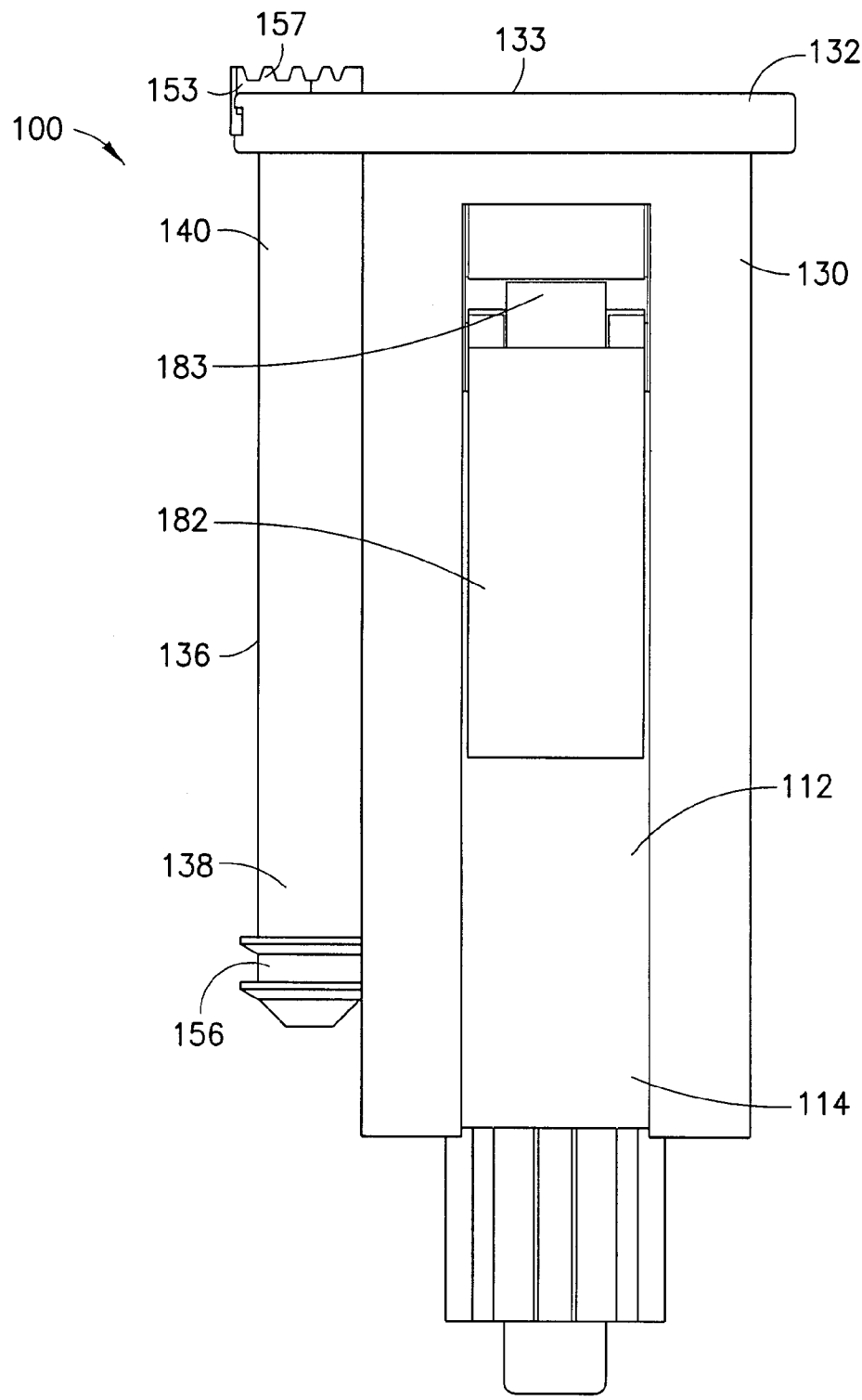
Figure 6C:
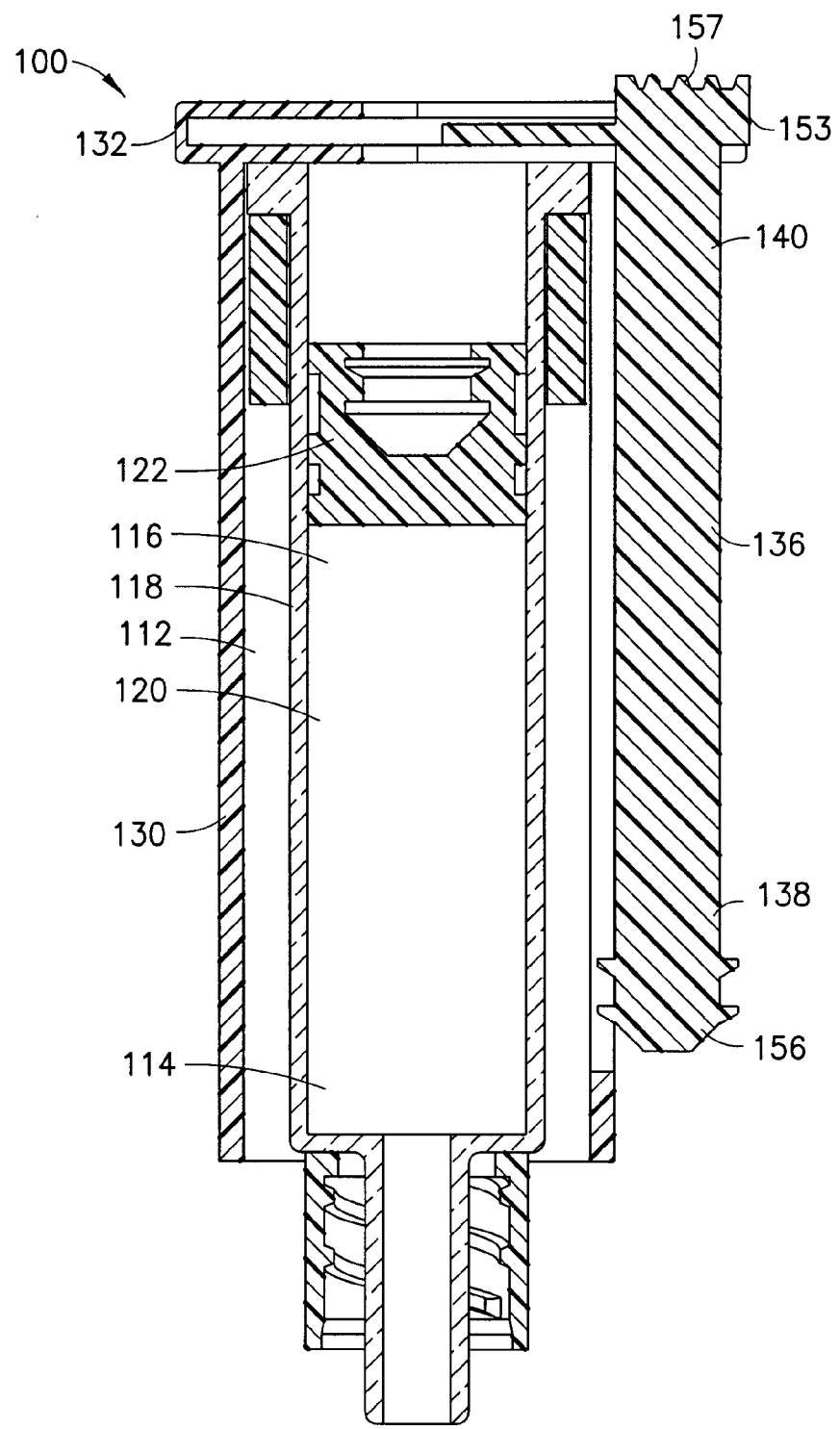
Figure 7A:
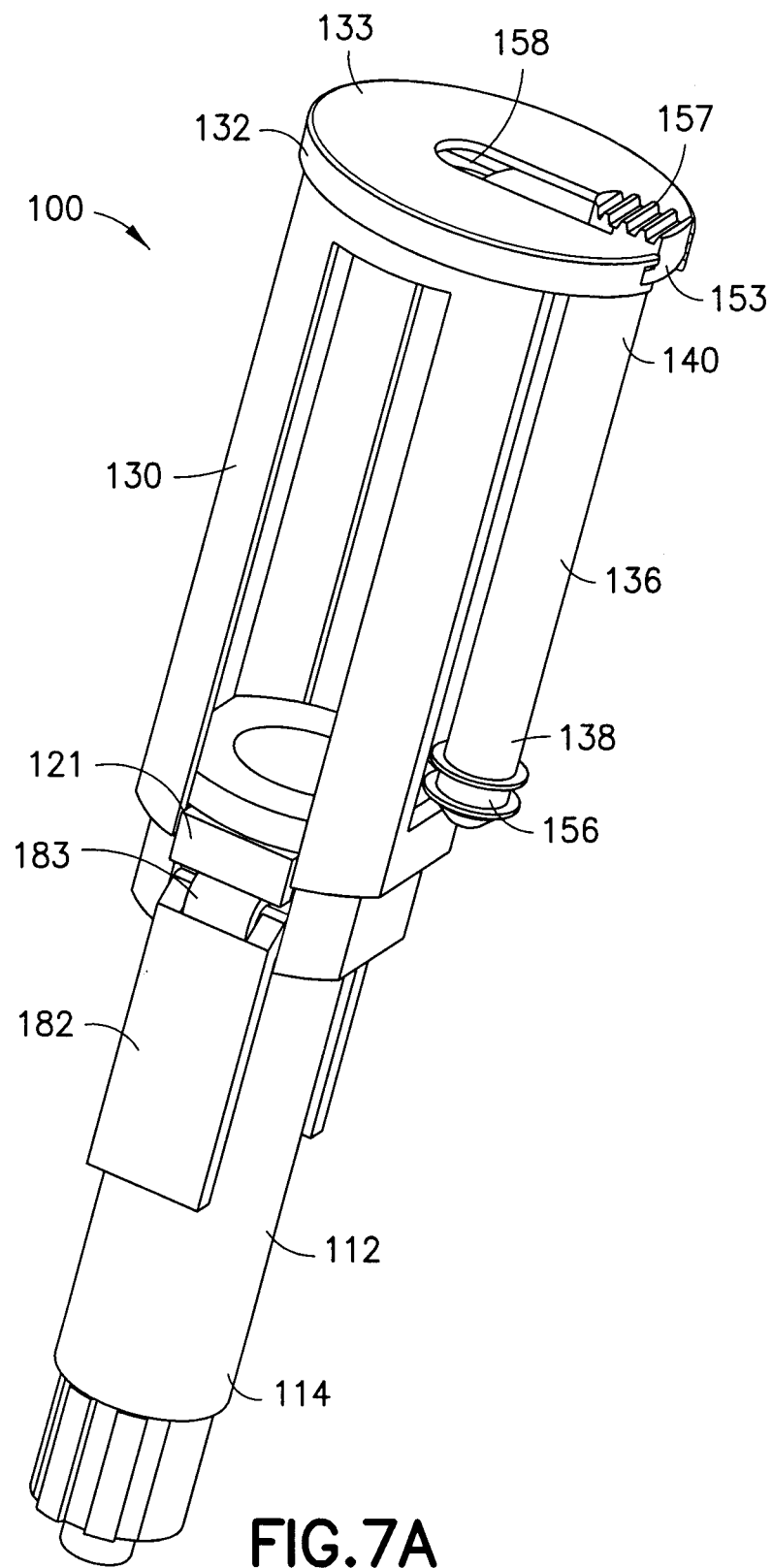
FIGS. 7A-7C are perspective, side elevation, and cross-sectional views of the syringe assembly of FIGS. 6A-6C with the sleeve in an expanded position in accordance with an embodiment of the present invention.
Figure 7B:
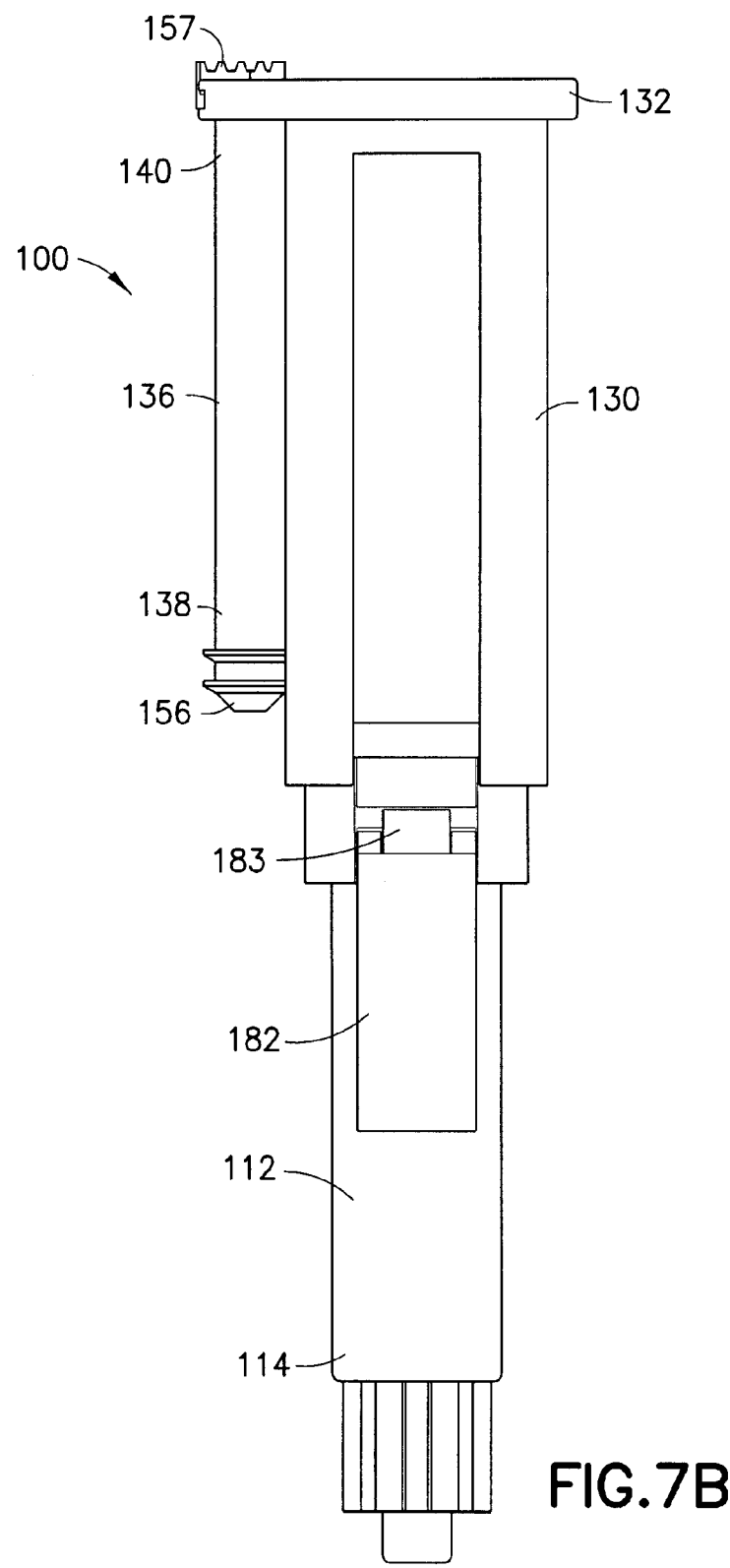
Figure 7C:
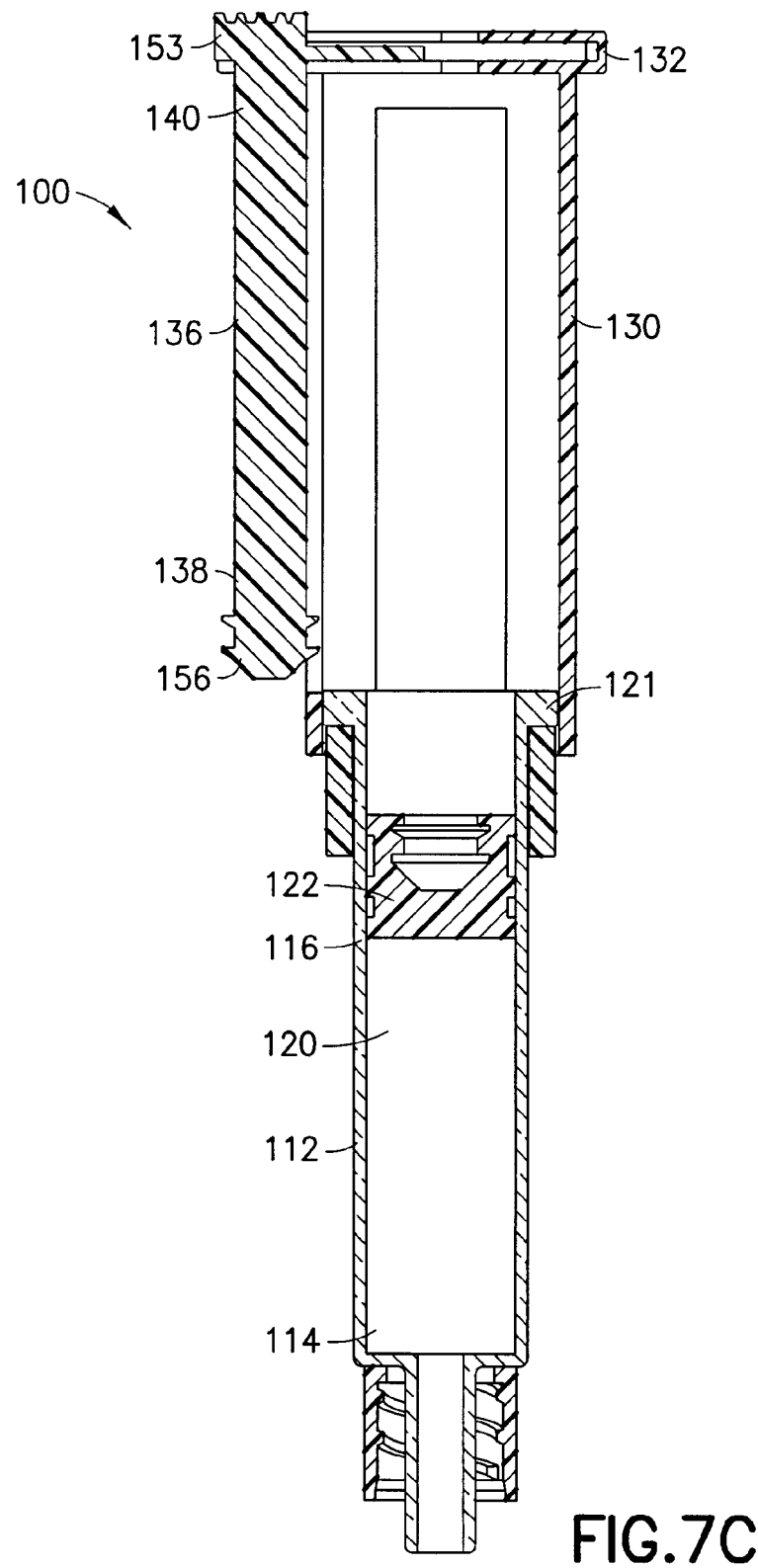
Figure 8A:
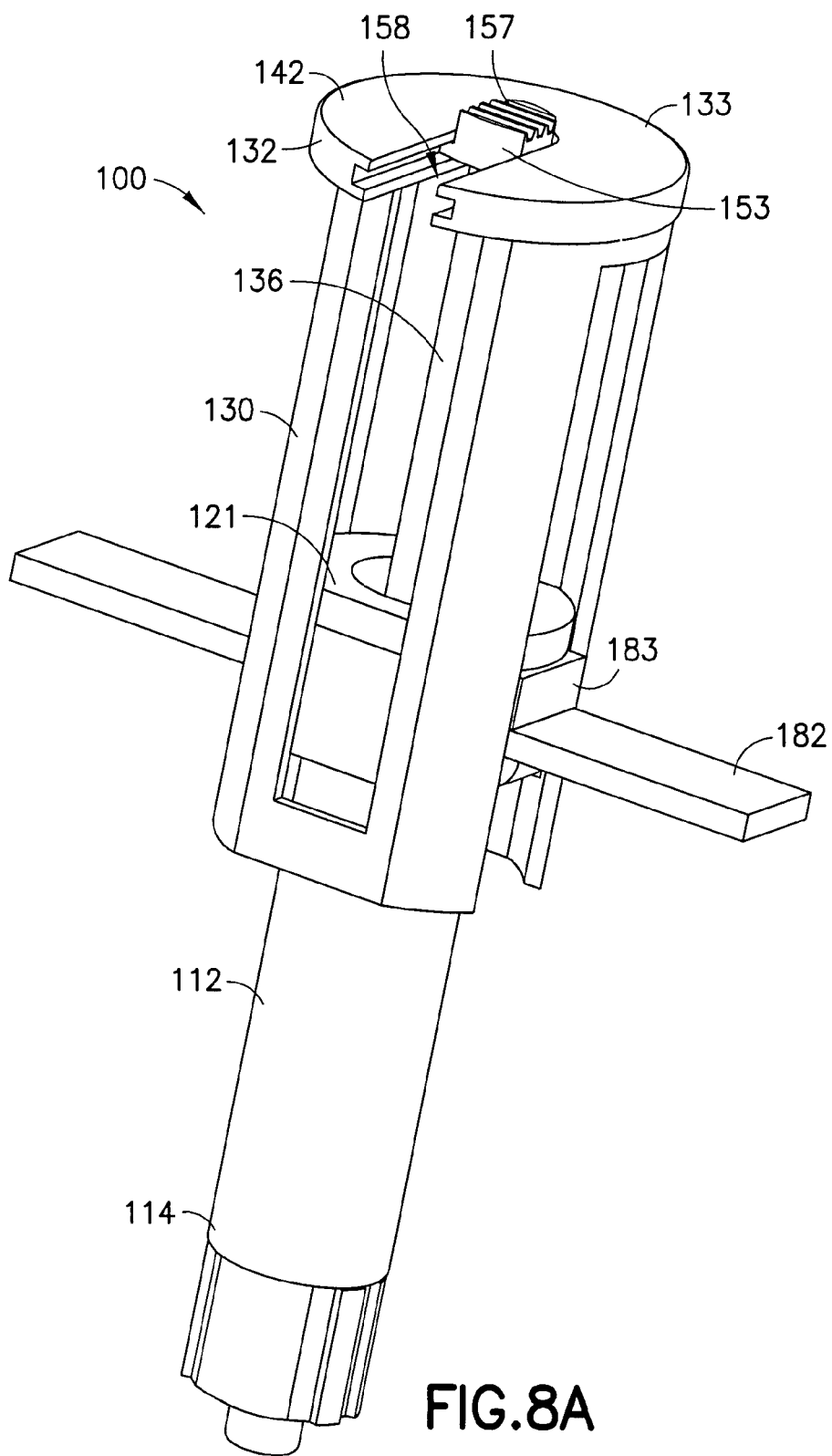
FIGS. 8A-8C are perspective, side elevation, and cross-sectional views of the syringe assembly of FIGS. 6A-6C with the plunger rod positioned in an activated, ready-to-use position in accordance with an embodiment of the present invention.
Figure 8B:
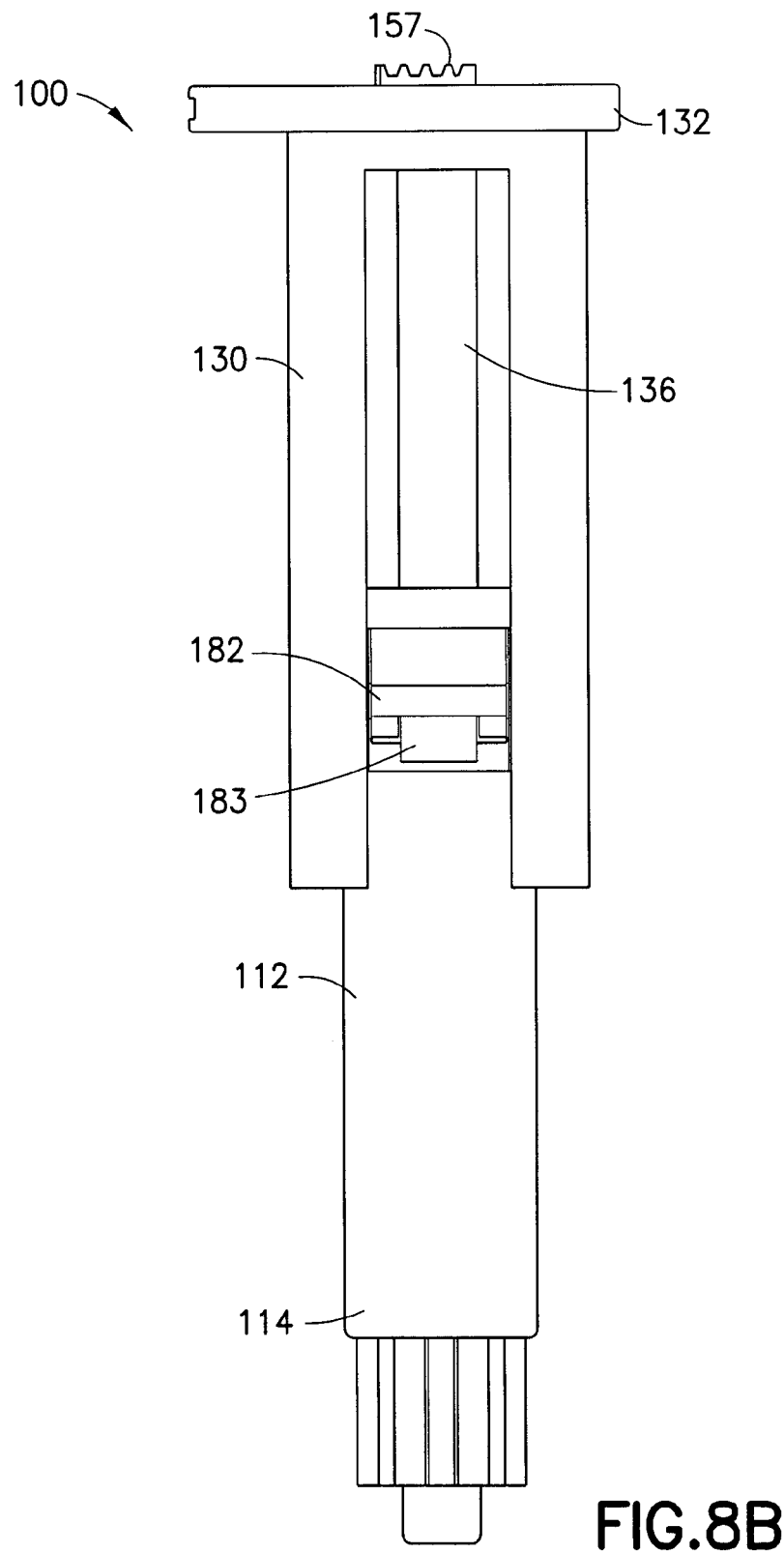
Figure 8C:
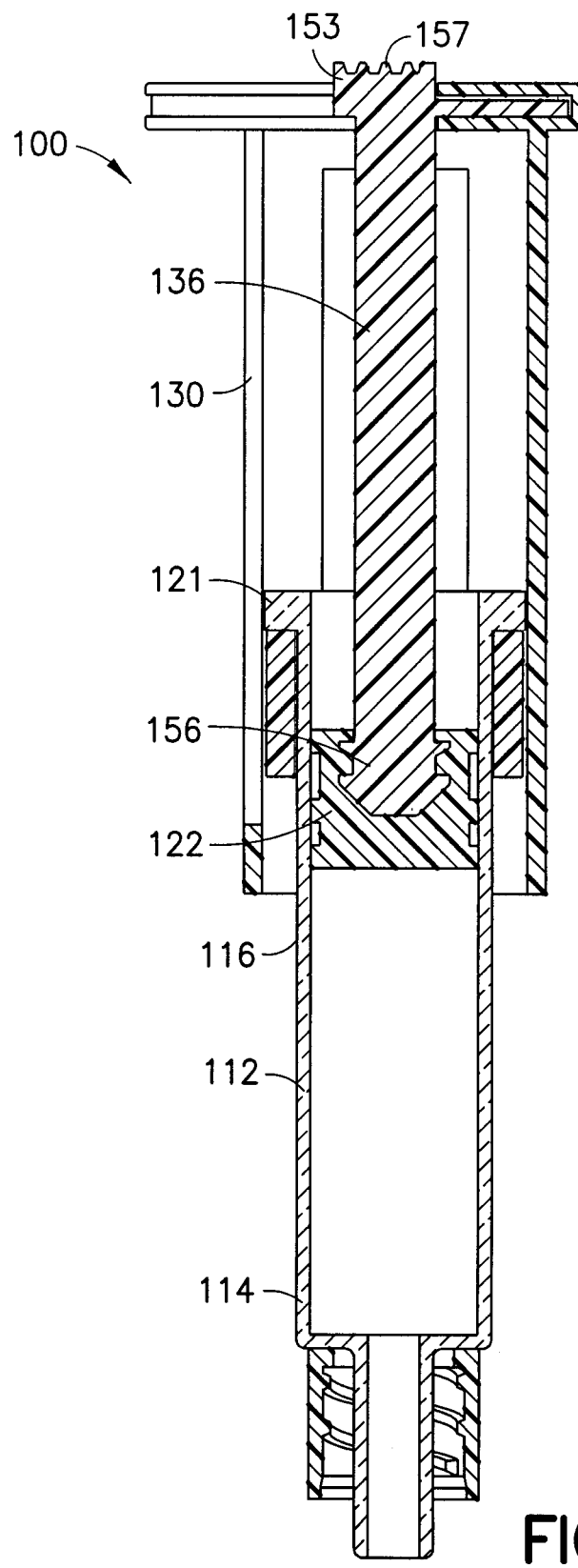
Figure 9A:
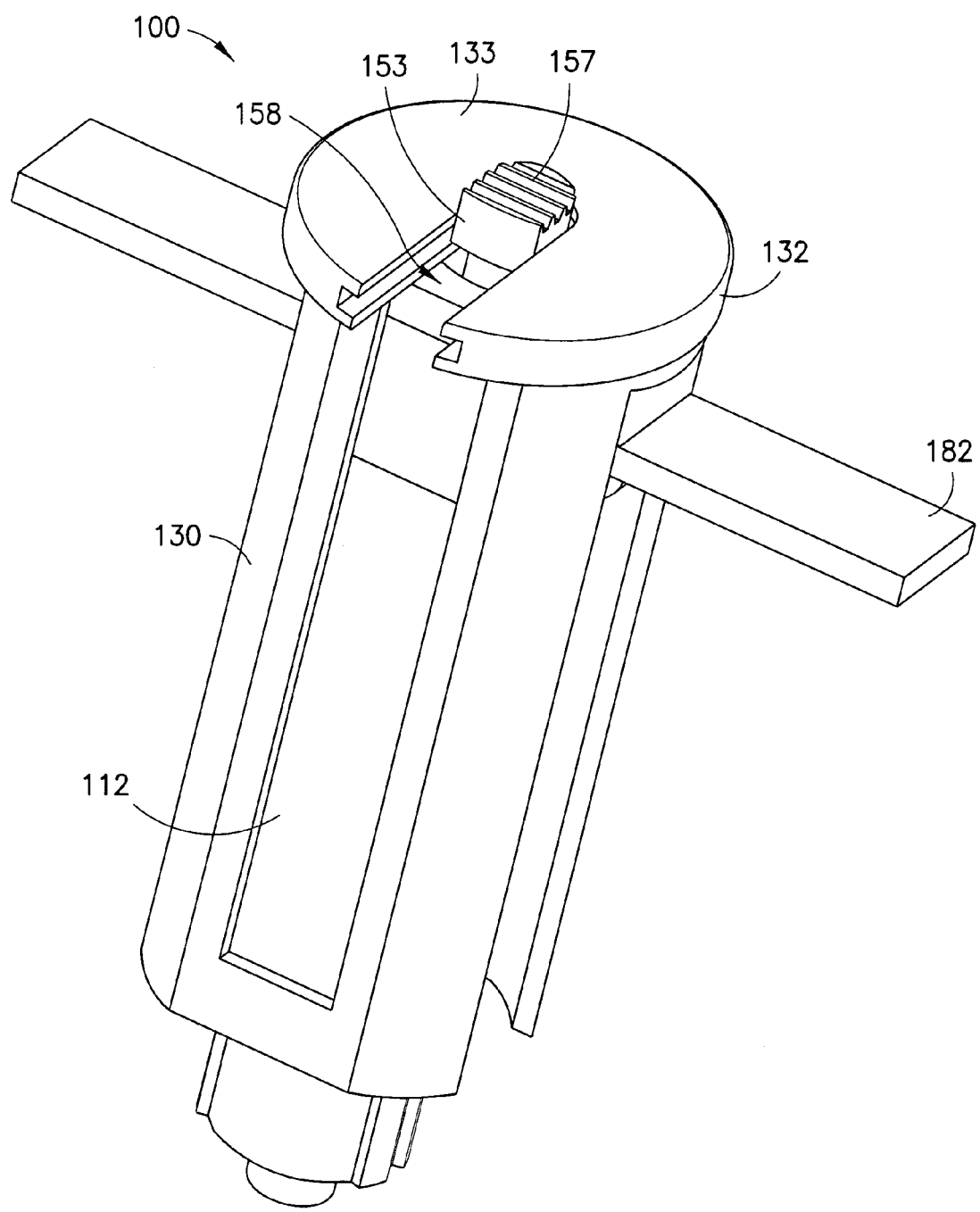
FIGS. 9A-9C are perspective, side elevation, and cross-sectional view of the syringe assembly of FIGS. 6A-6C in the final, used position in accordance with an embodiment of the present invention.
Figure 9B:
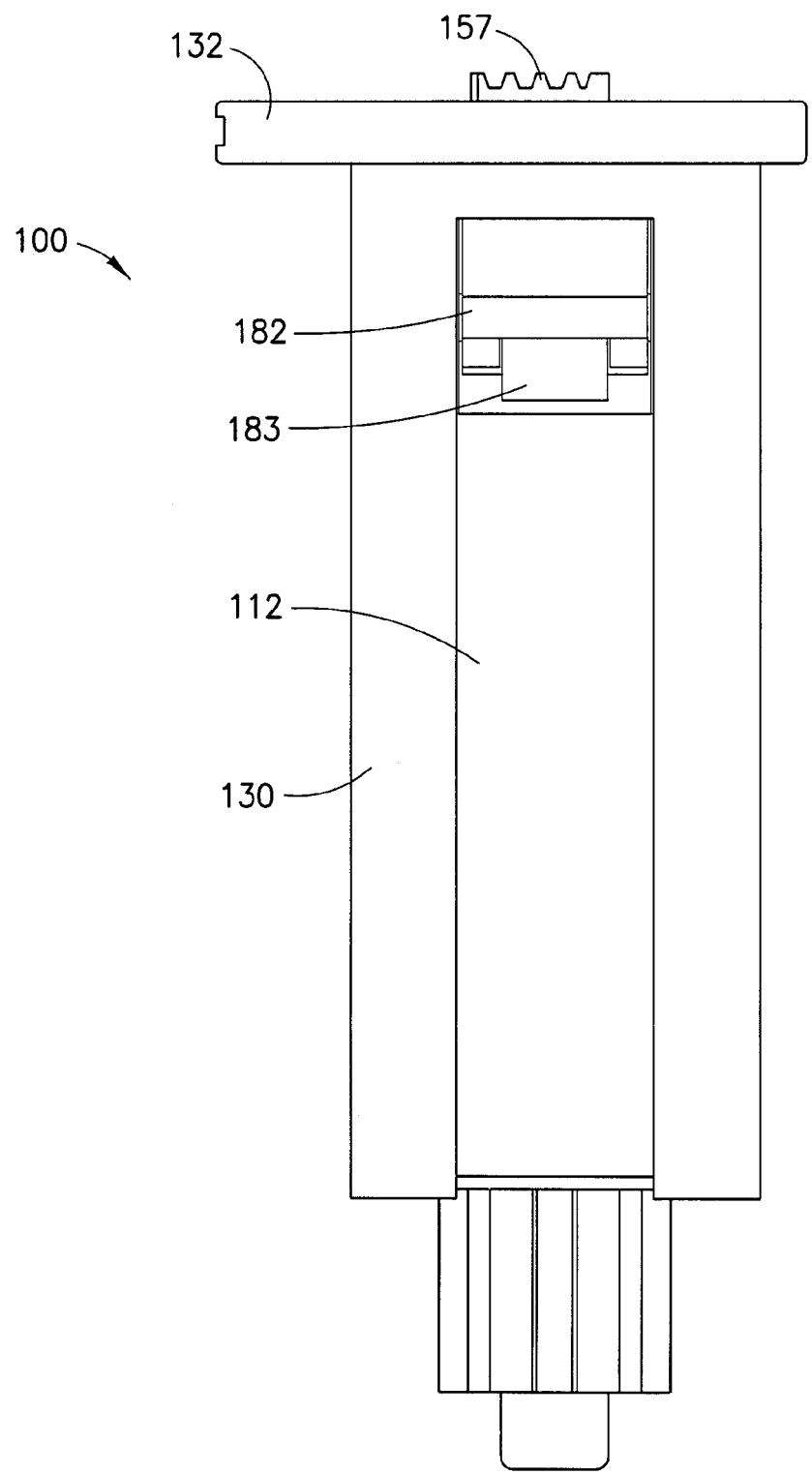
Figure 9C:
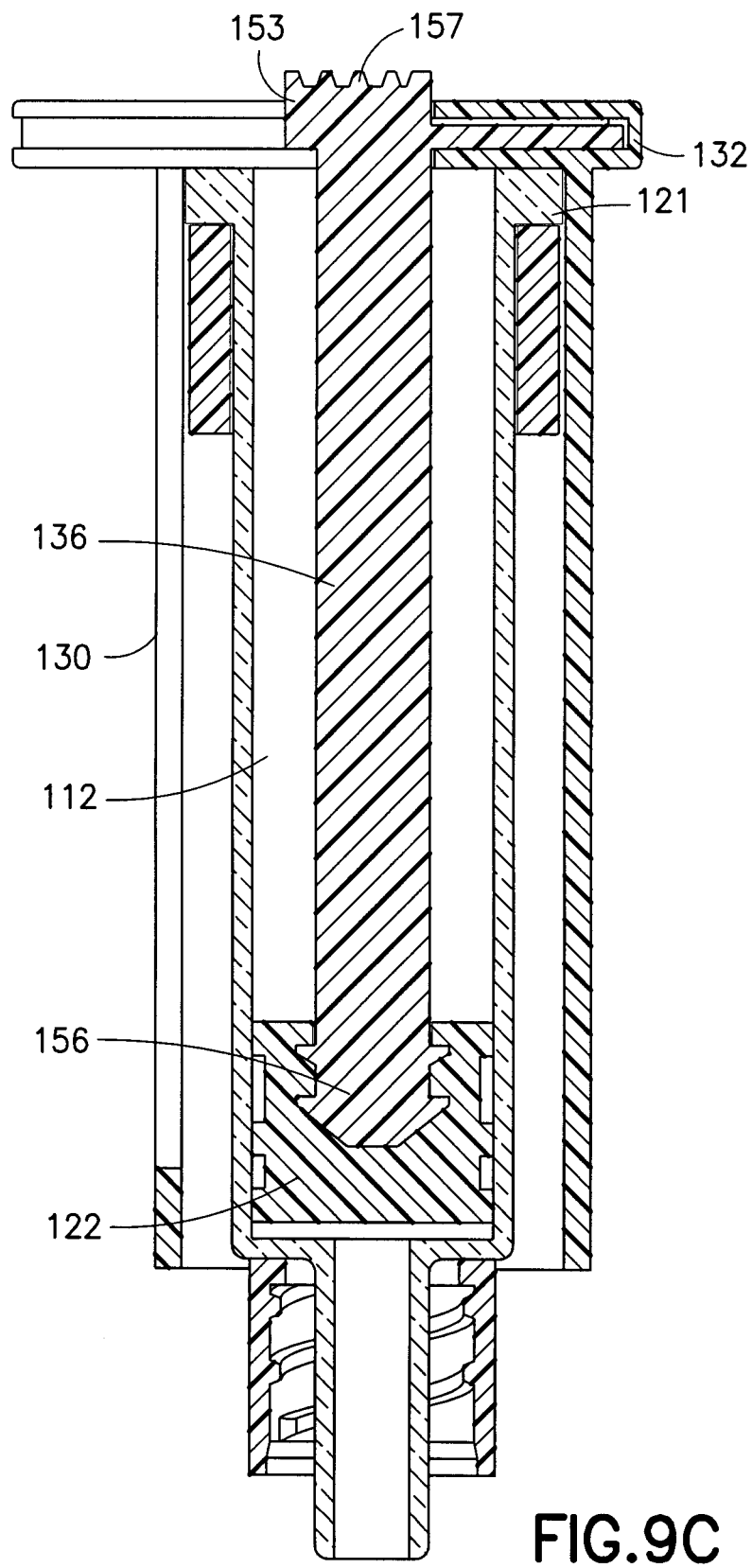

With continuing reference to FIGS. 6A-6C, 7A-7C, 8A-8C, and 9A-9C and with reference to FIG. 10, a sleeve 130 extends about the body of the syringe barrel 112 in a first or pre-use position. A cap 132 is integrally joined to the sleeve 130. The cap 132 can include a thumb press portion 142, as discussed above and is known in the art, upon which a user can apply a distally directed force during use of the syringe assembly 100. As illustrated in FIGS. 6A-6C, a plunger rod 136, including a first end 138 and a second end 140, is positioned alongside the sleeve 130 and syringe barrel 112 in this pre-use position. The plunger rod 136 can be integrally formed with the sleeve 130 or can extend alongside the sleeve 130. A portion of the sleeve 130 can be cut out or indented to receive the plunger rod 136. According to one design, the second end 140 can include a male connection member 153 which is associated with a female groove or opening 158 extending through the cap 132. At least a top portion 157 of this male connection member 153 can be accessible from a top surface 133 of the cap 132 so that upon proximal movement of the sleeve 130, as shown in FIGS. 7A-7C, a lateral force LF can be applied by a user to the top portion 157 of the male connection member 153 in the direction shown in FIG. 10 to cause the plunger rod 136 to move along the female groove 158. The top portion 157 of the male connection member 153 can have a roughened or serrated surface to provide a frictional surface for assisting the user in movement or actuation of the plunger rod 136. As shown in FIGS. 8A-8C, upon lateral movement of the plunger rod 136, the first end 138 of the plunger rod 136 including a connection member 156 comes into contact with and mates with the stopper 122. It can be appreciated that this connection member 156 on the plunger rod 136 can comprise either a male or a female mating member which can be configured to cooperate with a female or male mating member in either the stopper 122 or a stopper adapter (not shown) which is similar in design with the stopper adapter 44 discussed in detail above. Once the first end 138 of the plunger rod 136 is mated with and aligned with the stopper 122 or a stopper adapter, the plunger rod 136 is in the ready-to-use position, and can be activated to expel the syringe contents as shown in FIGS. 9A-9C.

Another feature of the present invention is an application flange 182 which is pivotally attached at 183 to the syringe barrel 112 or to the flange 121 of the syringe barrel 112. As shown in FIGS. 8A and 9A, this application flange 182 can be pivoted in an outward or radial direction with respect to the syringe barrel 112 or syringe assembly 100, to provide a grasping surface and assist the user during injection or expelling of the syringe contents.

With reference to FIG. 10, a removable dust shield 185 can be positioned adjacent the top surface 133 of the cap 132 to protect the syringe contents of a pre-filled syringe 100 from debris and contamination which could enter through the female groove 158 of the cap 132 or at any other location through the cap 132. As illustrated in FIGS. 11A and 11B, the syringe barrel 112 can include an undercut flange portion 188 and the cap 132 can be rotatable about the syringe barrel 112 during assembly to lock the cap 132 onto the syringe barrel 112 and to prevent inadvertent actuation of the sleeve 130. During operation, the cap 132 is rotated to unlock the cap 132 from the syringe flange 121 prior to movement of the cap 132 in the proximal direction. According to one design, the cap 132 can be rotated approximately 90 degrees to unlock the cap 132 from the syringe flange 121 prior to movement of the cap 132 in the proximal direction. A stop member, well known in the art, can be provided to limit a length of proximal movement of the sleeve 130 with respect to the syringe barrel 112 to prevent pull-out of the sleeve 130 and plunger rod 136 with respect to the syringe assembly 100.

It can be appreciated that each of the embodiments disclosed above result in a syringe assembly having a reduced footprint which is desirable in the packaging of the syringe assemblies as it requires less packaging. This reduced footprint provides for syringe assemblies having consistently sized profiles which allow for easy stacking and require less storage space, both of these features being desirable in a controlled storage environment.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention.

The invention claimed is:

1. A syringe assembly comprising:
    a syringe barrel having a first end, a second end, and a sidewall extending between the first and second ends defining a chamber;
    a stopper disposed within the chamber of the syringe barrel;
    a sleeve having a first end and a second end and extending at least partially about the syringe barrel;
    a cap associated with the second end of the sleeve; and
    a plunger rod having a first end and a second end, the first end associated with the cap, wherein the plunger rod is transitionable from a pre-use position, in which at least a portion of the second end of the plunger rod extends along a portion of the barrel sidewall, and a ready-to-use position in which the plunger rod is aligned with the stopper, wherein upon proximal movement of the sleeve in a direction away from the first end of the barrel, the plunger rod is configured for lateral movement with respect to the cap into the ready-to-use position.

2. The syringe assembly of claim 1, further comprising a stopper adapter associated with the stopper, and wherein the syringe barrel, stopper, and stopper adapter are oriented along a longitudinal axis of the syringe assembly.

3. The syringe assembly of claim 2, wherein the second end of the plunger rod comprises an attachment member configured for cooperation with the stopper adapter.

4. The syringe assembly of claim 1, wherein the first end of the plunger rod includes a slideable connection member for engaging a portion of the cap.

5. The syringe assembly of claim 4, wherein the cap includes a radially extending track for cooperating with the slideable connection member of the plunger rod.

6. The syringe assembly of claim 5, wherein the slideable connection member comprises one of a male connection member and a female connection member and the track comprises the other of a cooperating male connection member and a cooperating female connection member.

7. The syringe assembly of claim 5, wherein at least a portion of the plunger rod moves along the track upon the application of a lateral force to a portion of the plunger rod.

8. The syringe assembly of claim 1, wherein the sleeve includes a distal portion which encompasses a portion of the syringe barrel and further comprises at least one leg having a first end associated with the distal portion of the sleeve and a second end associated with the cap.

9. The syringe assembly of claim 7, wherein the plunger rod comprises a first portion associated with the distal portion of the sleeve and includes a stop, and a second portion associated with the cap, wherein upon proximal movement of the sleeve, the stop of the first portion cooperates with a syringe barrel flange to limit the proximal movement of the sleeve with respect to the syringe assembly.

10. The syringe assembly of claim 8, wherein the distal portion of the sleeve includes a stop for cooperating with a radially extending flange of the syringe barrel to limit the proximal movement of the sleeve with respect to the syringe assembly.

11. The syringe assembly of claim 6, wherein the slideable connection member comprises a male connection member and the track includes a female groove extending through the cap for cooperating with the male connection member, wherein at least a top portion of the male connection member is accessible from a top surface of the cap so that the application of a lateral force to the top portion of the male connection member causes the plunger rod to move along the groove and into contact with the stopper.

12. The syringe assembly of claim 11, including a removable dust shield positioned adjacent the top surface of the cap.

13. The syringe assembly of claim 12, wherein the syringe barrel further comprises an undercut flange portion and the cap is rotatable about the syringe barrel during assembly to engage the cap with the undercut flange portion to prevent inadvertent actuation.

14. The syringe assembly of claim 13, wherein the cap is rotated about the syringe barrel to disengage the cap from the undercut flange portion prior to movement of the cap in a proximal direction.

15. The syringe assembly of claim 12, further comprising a stop member integral with the sleeve to limit proximal movement of the cap with respect to the syringe assembly.

16. The syringe assembly of claim 1, further comprising a liquid within the chamber.

17. The syringe assembly of claim 1, further comprising a tamper indicating label disposed about a portion of the syringe assembly.

18. The syringe assembly of claim 1, further comprising a medication or drug disposed within the chamber of the syringe barrel.

19. A telescopic plunger rod and cap assembly for use with a syringe assembly, the plunger rod and cap assembly comprising:
    a sleeve having a first end and a second end and configured for telescopic movement with respect to a syringe barrel;
    a cap associated with the second end of the sleeve; and
    a plunger rod having a first end and a second end, the first end associated with the cap wherein the plunger rod is transitionable from a pre-use position, in which at least a portion of the second end of the plunger rod is configured to extend along a portion of the barrel, and a ready-to-use position in which the plunger rod is aligned with a stopper, wherein upon relative movement of the sleeve with respect to the syringe barrel, the plunger rod is configured for lateral movement with respect to the cap into the ready-to-use position.

20. The plunger rod and cap assembly of claim 19, wherein the second end of the plunger rod includes an attachment member configured for cooperation with the stopper and wherein the first end of the plunger rod includes a slideable connection member.

21. The plunger rod and cap assembly of claim 20, wherein the slideable connection member comprises one of a male connection member and a female connection member and a track comprises the other of a cooperating male connection member and a cooperating female connection member.

22. The plunger rod and cap assembly of claim 19, wherein the sleeve includes a distal portion which encompasses a portion of the syringe barrel and at least one leg having a first end associated with the distal portion of the sleeve and a second end associated with the cap.

23. The plunger rod and cap assembly of claim 22, wherein the plunger rod comprises a first portion associated with the distal portion of the sleeve and includes a stop, and a second portion associated with the cap, wherein upon proximal movement of the sleeve with respect to the syringe barrel, the stop of the first portion cooperates with a syringe barrel flange to limit the proximal movement of the sleeve with respect to the syringe assembly.

24. The plunger rod and cap assembly of claim 22, wherein the distal portion of the sleeve includes a stop surface for cooperating with a syringe barrel flange to limit the proximal movement of the sleeve with respect to the syringe assembly.

25. A syringe assembly comprising:
    a syringe barrel having a proximal end, a distal end, and a sidewall extending between the proximal and distal ends defining a chamber;
    a stopper disposed within the chamber of the syringe barrel;
    a sleeve at least partially disposed about the syringe barrel; and
    a plunger rod having a first end and second end, both the first end and the second end being integral with the sleeve in a first pre-use position and one of the first end and the second end being laterally advanceable with respect to a portion of the sleeve to integrally engage the stopper in a second ready-to-use position.

26. The syringe assembly of claim 25, wherein the plunger rod moves from the first to the second position upon proximal movement of the sleeve with respect to the barrel.

27. The syringe assembly of claim 26, wherein the plunger rod is movable in a lateral direction with respect to a longitudinal axis of the sleeve upon proximal movement of the sleeve with respect to the barrel.

28. The syringe assembly of claim 25, including a stopper adapter associated with the stopper and wherein one of the first end and second end of the plunger rod includes an attachment member configured for cooperation with the stopper adapter when the stopper is in the second position.

* * * * *